United States Patent
Oshiro et al.

[11] Patent Number: 6,133,264
[45] Date of Patent: Oct. 17, 2000

[54] CARBOSTYRIL DERIVATIVES FOR INHIBITING SKIN ERYTHEMA AND/OR SKIN PIGMENTATION

[75] Inventors: Yasuo Oshiro; Takao Nishi, both of Tokushima; Keiichi Kuwahara, Ako; Kozo Watanabe, Kobe, all of Japan

[73] Assignee: Otsuka Pharmaceutical Co., Ltd., Tokyo, Japan

[21] Appl. No.: 09/485,454

[22] PCT Filed: Aug. 18, 1998

[86] PCT No.: PCT/JP98/03657

§ 371 Date: Feb. 10, 2000

§ 102(e) Date: Feb. 10, 2000

[87] PCT Pub. No.: WO99/09011

PCT Pub. Date: Feb. 25, 1999

[30] Foreign Application Priority Data

Aug. 19, 1997 [JP] Japan ................................. 9-222431

[51] Int. Cl.[7] ...................... A61K 31/5377; A61D 17/00; C07D 401/02
[52] U.S. Cl. ..................... 514/235.2; 544/58.6; 544/128; 544/363; 546/157; 546/158
[58] Field of Search ............................ 544/128; 546/158; 514/235.2

[56] References Cited

FOREIGN PATENT DOCUMENTS

| 0 081 782 | 6/1983 | European Pat. Off. . |
| 0 467 325 | 1/1992 | European Pat. Off. . |
| 0 638 571 | 2/1995 | European Pat. Off. . |
| 4-234386 | 8/1992 | Japan . |
| WO 96/02508 | 2/1996 | WIPO . |
| WO 97/03066 | 1/1997 | WIPO . |
| WO 97/44037 | 11/1997 | WIPO . |
| WO 97/44321 | 11/1997 | WIPO . |

OTHER PUBLICATIONS

D. Blondet et al., "Convenient Synthesis of 6–Methyl, 8–Methyl and 6,8–Dimethyl Derivatives of 5–Hydroxy–1,2,3,4–Tetrahydro–2–Quinolinone", Chemical Abstracts, vol. 119, No. 9, Abstract No. 95292j, (1993).

Primary Examiner—Robert W. Ramsuer
Attorney, Agent, or Firm—Finnegan, Henderson, Farabow, Garrett & Dunner, L.L.P.

[57] ABSTRACT

The present invention provides an agent for inhibiting skin erythema and/or skin pigmentation, containing at least one selected from the group consisting of the carbostyril derivative and salt thereof represented by the general formula,

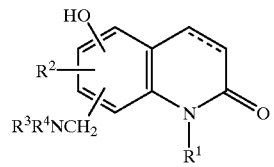

(wherein $R^1$ is a hydrogen atom, a lower alkyl group or the like; $R^2$ is a hydrogen atom, a lower alkyl group, a lower alkoxy group or the like; $R^3$ and $R^4$ are lower alkyl groups which may have hydroxyl groups as substituents or the like; the carbon—carbon bond between 3- and 4-positions in the carbostyril skeleton is a single bond or double bond).

24 Claims, No Drawings

CARBOSTYRIL DERIVATIVES FOR INHIBITING SKIN ERYTHEMA AND/OR SKIN PIGMENTATION

This application is a 371 of PCT/JP98/03657 filed Aug. 18, 1998.

TECHNICAL FIELD

The present invention relates to carbostyril derivatives and agents for inhibiting skin erythema and/or skin pigmentation containing, as the effective ingredient, said carbostyril derivative.

BACKGROUND ART

JP-A-4-234386 discloses carbostyril derivatives represented by the general formula (A),

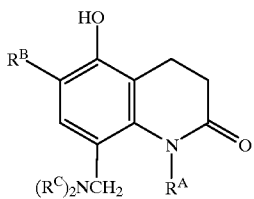

(A)

(wherein $R^A$ is a hydrogen atom or a lower alkyl group; $R^B$ is a hydrogen atom, a lower alkyl group or a lower alkoxy group; and $R^C$ is a lower alkyl group respectively) which can be used as intermediates for preparing other carbostyril derivatives used for treating cardiovascular diseases.

Additionally, WO 93/22317 discloses carbostyril derivatives represented by the general formula (B),

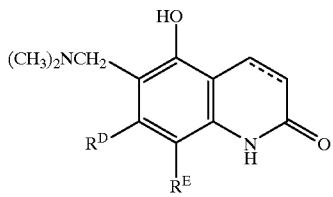

(B)

(wherein $R^D$ and $R^E$ are each the same or different from each other and are hydrogen atoms, lower alkyl groups or lower alkoxy groups; and the carbon—carbon bond between 3- and 4-positions in the carbostyril skeleton is a single bond or double bond) which can be used as intermediates for preparing quinoline derivatives used for remedy for cardiac diseases.

However, these prior art references disclose only that the above-mentioned carbostyril derivatives can be used as intermediates for preparing blocking agents of adrenaline β-receptor or antiarrhythmic drugs. Thus, above-mentioned prior art references do not disclose at all that these carbostyril derivatives per se possess whatever pharmacological activities.

Furthermore, WO 97/44037 and WO 97/44321 disclose quinoline compounds as antagonists of gonadotropin-releasing hormone, and WO 97/03066 discloses substituted benzolactam compounds as substance P antagonist. In fact that these quinoline compounds and substituted benzolactam compounds involve carbostyril skeleton in their molecular structures. However, these compounds are quite different from the carbostyril derivatives of the present invention in both chemical structures and usages.

DISCLOSURE OF THE INVENTION

The present inventors have found the fact that at least one of the compound selected from the group consisting of carbostyril derivatives represented by the general formula (1) and salts thereof including the above-mentioned known compounds possesses activities for inhibiting skin erythema (sunburn) and/or skin pigmentation. Such pharmacological activities could not been anticipated from the usefulnesses being disclosed in these prior art references. Thus the present invention has been successfully established on the basis of said finding.

The present invention relates to agents for inhibiting skin erythema (sunburn) and/or skin pigmentation containing, as the effective ingredient, at least one selected from the group consisting of carbostyril derivatives and salts thereof represented by the general formula (1),

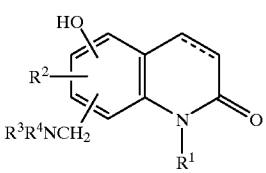

(1)

(wherein $R^1$ is a hydrogen atom, a lower alkyl group or a lower alkenyl group; $R^2$ is a hydrogen atom, a lower alkyl group, a lower alkoxy group, a lower alkenyloxy group, a lower alkenyl group or a tetrahydropyranyloxy group; $R^3$ and $R^4$ are the same or different from each other, and each is a lower alkyl group which may have hydroxyl groups as substituents; further $R^3$ and $R^4$ may form, together with the adjacent nitrogen atom, further with or without additional nitrogen atom, sulfur atom or oxygen atom, a 5- or 6-membered saturated heterocyclic group which may have substituents selected from the group consisting of a lower alkyl group and a lower alkanoy group; the carbon—carbon bond between 3- and 4-positions in the carbostyril skeleton is a single bond or double bond).

Nowadays, vitamins such as vitamin E, ascorbic acid and the like; natural substances such as arbutin, kojic acid and the like are used as the effective ingredients in cosmetics for preventing sunburn and suntan being caused by exposure to UV rays and the sun light, as well as for the purpose to effect bleaching the skin pigmentation such as spots and ephelides. However, these vitamins and natural substances are difficult to handle becaued they are unstable to oxygen, light, heat, alkalis and acids. Also the effects for preventing sunburn and bleaching skin pigmentation performed by these vitamins and natural substances are not good enough.

Under such circumstances, it is expected and desired to develop a new compound which is stable to oxygen, light, heat, alkalis and acids, also having excellent effects for preventing sunburn as well as for bleaching skin pigmentation. For the purpose to use such a new compound as an effective ingredient in quasi-drugs and cosmetics which has to be applied to the human body for a long period of time, said new compound should not have any irritant action to the skin and highly safety to the skin without inducing cutaneous allergy. Also, such new compound is desired not to give any adverse effect to the circulation system and central nervous system at the concentration in pharmaceutical applications.

The carbostyril derivatives represented by the general formula (1) and salts thereof can entirely meet the above-mentioned requirements. Thus, the carbostyril derivatives and salts thereof of the present invention are stable to the light, heat, alkalis and acids and the like, as well as having excellent effects for preventing sunburn of the skin and for bleaching the skin pigmentation. Furthermore, the carbostyril derivatives and salts thereof of the present invention do not have any irritant action to the skin with highly safety to the skin without inducing cutaneous allergy. Additionally, the carbostyril derivatives and salts thereof are easily soluble in water.

Similar to vitamin E, the carbostyril derivatives and salts thereof of the present invention can scavenge diphenylpicrylhydrazide (DPPH) which is a model compound of lipoperoxide, and besides, the carbostyril derivatives of the present invention can inhibit the formation of erythema (sunburn) caused by irradiation of ultraviolet rays. Therefore, the carbostyril derivatives and salts thereof of the present invention are useful as agents for preventing and treating various dermatopathies and dermatitises caused by irradiation of ultraviolet rays, and by contact with oxygen radicals or lipoperoxides.

The carbostyril derivatives and salts thereof of the present invention can be clearly inhibit the skin pigmentation caused by irradiation of ultraviolet ray. Therefore, the carbostyril derivatives and salts thereof of the present invention are useful as the active ingredient to be contained in cosmetics, quasi-drugs, pharmaceutical preparations and the like for preventing sunburn and suntan caused by excessive exposures of ultraviolet rays and sun light, and for preventing and treating skin pigmentations such as spots and ephelides.

Among carbostyril derivatives and salts thereof represented by the general formula (1), the carbostyril derivatives and salts thereof represented by the general formula (2),

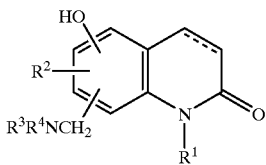

(2)

(wherein $R^1$ is a hydrogen atom, a lower alkyl group or a lower alkenyl group; $R^2$ is a hydrogen atom, a lower alkyl group, a lower alkoxy group, a lower alkenyloxy group, a lower alkenyl group or a tetrahydropyranyloxy group; $R^3$ and $R^4$ are the same or different from each other, and each is a lower alkyl group which may have hydroxyl group as substituents; further $R^3$ and $R^4$ may form, together with the adjacent nitrogen atom, further with or without additional nitrogen atom, sulfur atom or oxygen atom, a 5- or 6-membered saturated heterocyclic group which may have substituents selected from the group consisting of a lower alkyl group and lower alkanoyl group; the carbon—carbon bond between 3- and 4-positions in the carbostyril skeleton is a single bond or double bond; provided that when both $R^3$ and $R^4$ are lower alkyl groups, then $R^2$ should be neither a hydrogen atom, a lower alkyl group nor a lower alkoxy group) are novel compounds which have not been known in any prior art literature.

Concrete examples of the substituents shown in the general formula (1) are as follows.

As to the lower alkyl groups, a straight-chain or branched-chain alkyl group having 1 to 6 carbon atoms, such as methyl, ethyl, propyl, isopropyl, butyl, isobutyl, tert-butyl, pentyl, hexyl groups and the like can be exemplified.

As to the lower alkenyl group, a straight-chain or branched-chain alkenyl group having 2 to 6 carbon atoms, such as vinyl, allyl, 2-butenyl, 3-butenyl, 1-methylallyl, 2-pentenyl, 3-methyl-2-butenyl, 2-hexenyl groups and the like can be exemplified.

As to the lower alkoxy group, a straight-chain or branched-chain alkoxy group having 1 to 6 carbon atoms, such as methoxy, ethoxy, propoxy, isopropoxy, butoxy, tert-butoxy, pentyloxy, hexyloxy groups and the like can be exemplified.

As to the alkenyloxy group, a straight-chain or branched-chain alkenyloxy group having 2 to 6 carbon atoms, such as vinyloxy, allyloxy, 2-butenyloxy, 3-butenyloxy, 1-methylallyloxy, 2-pentenyloxy, 3-methyl-2-butenyloxy, 2-hexenyloxy groups and the like can be exemplified.

As to the lower alkyl group which may have hydroxyl groups as substituents, a straight-chain or branched-chain alkyl group having 1 to 6 carbon atoms, which may have 1 to 3 hydroxyl groups as substituents, such as hydroxymethyl, 2-hydroxyethyl, 3-hydroxypropyl, 2-hydroxypropyl, 2-hydroxyisopropyl, 2-hydroxybutyl, 2-hydroxybutyl, 4-hydroxybutyl, 2-hydroxypentyl, 3-hydroxypentyl, 4-hydroxypentyl, 5-hydroxypentyl, 2-hydroxyhexyl, 3-hydroxyhexyl, 4-hydroxyhexyl, 6-hydroxyhexyl, 1-methyl-2-hydroxyethyl, 1,1-dimethyl-2-hydroxyethyl, 1,2-dihydroxyethyl, 2,2-dihydroxyethyl, 1,3-dihydroxypropyl, 2,3-dihydroxypropyl, 1,2,3-trihydroxypropyl, 1,4-dihydroxybutyl, 2,4-dihydroxybutyl, 3,4-dihydroxybutyl, 1,2-dihydroxybutyl, 2,3-dihydroxybutyl, 1,3-dihydroxybutyl, 2,2-dihydroxybutyl, 1,2,3-trihydroxybutyl, 2,3,4-trihydroxybutyl, 2,3-dihydroxypentyl, 3,4-dihydroxypentyl, 3,5-dihydroxypentyl, 3,4,5-trihydroxypentyl, 2,4,5-trihydroxypentyl, 2,3-dihydroxyhexyl, 3,4-dihydroxyhexyl, 3,5-dihydroxyhexyl, 3,4,5-trihydroxyhexyl, 2,4,5-trihydroxyhexyl and the like can be exemplified.

As to the 5- or 6-membered saturated heterocyclic group which is formed by combining $R^3$ and $R^4$ to each other together with the adjacent nitrogen atom, further with or without additional nitrogen atom, sulfur atom or oxygen atom, examples are pyrrolidinyl, piperidinyl, piperazinyl, morphorino, thiomorphorino groups and the like.

As to the above-mentioned heterocyclic group having substituents selected from the group consisting of a lower alkyl group and a lower alkanoyl group, a heterocyclic group having 1 to 3 substituents selected from the group consisting of a straight-chain or branched-chain alkyl group having 1 to 6 carbon atoms and a straight-chain or branched-chain alkanoyl group having 1 to 6 carbon atoms, there can be exemplified 4-methylpiperazinyl, 3,4-dimethylpiperazinyl, 3-ethylpyrrolidinyl, 2-propylpyrrolidinyl, 3,4,5-trimethylpiperidinyl, 4-butylpiperidinyl, 3-pentylmorpholino, 4-hexylpiperazinyl, 3-methylthiomorpholino, 4-formylpiperazinyl, 4-acetylpiperazinyl, 4-acetylpiperidinyl, 3-propionylmorpholino, 2-butylthiomorpholino, 3-acetylpyrrolidinyl groups and the like.

As to the lower alkanoyl group, a straight-chain or branched-chain alkanoyl group having 1 to 6 carbon atoms, such as formyl, acetyl, propionyl, butyryl, isobutyryl, pentanoyl, tert-butylcarbonyl, hexanoyl groups can be exemplified.

The carbostyril derivatives of the present invention represented by the above-mentioned general formula (1) involve the following compounds as various embodiments.
1) A carbostyril derivative represented by the above-mentioned general formula (1) and salt thereof, wherein R$^1$ and R$^2$ are hydrogen atoms; and R$^3$ and R$^4$ are lower alkyl groups which may have hydroxyl groups as substituents.

2) A carbostyril derivative represented by the above-mentioned general formula (1) and salt thereof, wherein R$^1$ is a hydrogen atom; R$^2$ is a lower alkyl group; and R$^3$ and R$^4$ are lower alkyl groups which may have hydroxyl groups as substituents.

3) A carbostyril derivative represented by the above-mentioned general formula (1) and salt thereof, wherein R$^1$ is a hydrogen atom; R$^2$ is a lower alkoxy group; and R$^3$ and R$^4$ are lower alkyl groups which may have hydroxyl groups as substituents.

4) A carbostyril derivative represented by the above-mentioned general formula (1) and salt thereof, wherein R$^1$ is a hydrogen atom; R$^2$ is a lower alkenyloxy group; and R$^3$ and R$^4$ are lower alkyl groups which may have hydroxyl groups as substituents.

5) A carbostyril derivative represented by the above-mentioned general formula (1) and salt thereof, wherein R$^1$ is a hydrogen atom; R$^2$ is a lower alkenyl group; and R$^3$ and R$^4$ are lower alkyl groups which may have hydroxyl groups as substituents.

6) A carbostyril derivative represented by the above-mentioned general formula (1) and salt thereof, wherein R$^1$ is a lower alkyl group; R$^2$ is a hydrogen atom; and R$^3$ and R$^4$ are lower alkyl groups which may have hydroxyl groups as substituents.

7) A carbostyril derivative represented by the above-mentioned general formula (1) and salt thereof, wherein R$^1$ and R$^2$ are lower alkyl groups; and R$^3$ and R$^4$ are lower alkyl groups which may have hydroxyl groups as substituents.

8) A carbostyril derivative represented by the above-mentioned general formula (1) and salt thereof, wherein R$^1$ is a lower alkyl group; R$^2$ is a lower alkoxy group; and R$^3$ and R$^4$ are lower alkyl groups which may have hydroxyl groups as substituents.

9) A carbostyril derivative represented by the above-mentioned general formula (1) and salt thereof, wherein R$^1$ is a lower alkyl group; R$^2$ is a lower alkenyloxy group; and R$^3$ and R$^4$ are lower alkyl groups which may have hydroxyl groups as substituents.

10) A carbostyril derivative represented by the above-mentioned general formula (1) and salt thereof, wherein R$^1$ is a lower alkyl group; R$^2$ is a lower alkenyl group; and R$^3$ and R$^4$ are lower alkyl groups which may have hydroxyl groups as substituents.

11) A carbostyril derivative represented by the above-mentioned general formula (1) and salt thereof, wherein R$^1$ is a lower alkenyl group; R$^2$ is a hydrogen atom; and R$^3$ and R$^4$ are lower alkyl groups which may have hydroxyl groups as substituents.

12) A carbostyril derivative represented by the above-mentioned general formula (1) and salt thereof, wherein R$^1$ is a lower alkenyl group; R$^2$ is a lower alkyl group; and R$^3$ and R$^4$ are lower alkyl groups which may have hydroxyl groups as substituents.

13) A carbostyril derivative represented by the above-mentioned general formula (1) and salt thereof, wherein R$^1$ is a lower alkenyl group; R$^2$ is a lower alkoxy group; and R$^3$ and R$^4$ are lower alkyl groups which may have hydroxyl groups as substituents.

14) A carbostyril derivative represented by the above-mentioned general formula (1) and salt thereof, wherein R$^1$ is a lower alkenyl group; R$^2$ is a lower alkenyloxy group; and R$^3$ and R$^4$ are lower alkyl groups which may have hydroxyl groups as substituents.

15) A carbostyril derivative represented by the above-mentioned general formula (1) and salt thereof, wherein R$^1$ and R$^2$ are lower alkenyl groups; and R$^3$ and R$^4$ are lower alkyl groups which may have hydroxyl groups as substituents.

16) A carbostyril derivative represented by the above-mentioned general formula (1) and salt thereof, wherein R$^1$ and R$^2$ are hydrogen atoms; and R$^3$ and R$^4$ may form, together with the adjacent nitrogen atom, further with or without additional nitrogen atom, sulfur atom or oxygen atom, a 5- or 6-membered heterocyclic group which may have substituents selected from the group consisting of a lower alkyl group and a lower alkanoyl group.

17) A carbostyril derivative represented by the above-mentioned general formula (1) and salt thereof, wherein R$^1$ is a hydrogen atom; R$^2$ is a lower alkyl group; and R$^3$ and R$^4$ may form, together with the adjacent nitrogen atom, further with or without additional nitrogen atom, sulfur atom or oxygen atom, a 5- or 6-membered heterocyclic group which may have substituents selected from the group consisting of a lower alkyl group and a lower alkanoyl group.

18) A carbostyril derivative represented by the above-mentioned general formula (1) and salt thereof, wherein R$^1$ is a hydrogen atom; R$^2$ is a lower alkoxy group; and R$^3$ and R$^4$ may form, together with the adjacent nitrogen atom, further with or without additional nitrogen atom, sulfur atom or oxygen atom, a 5- or 6-membered heterocyclic group which may have substituents selected from the group consisting of a lower alkyl group and a lower alkanoyl group.

19) A carbostyril derivative represented by the above-mentioned general formula (1) and salt thereof, wherein R$^1$ is a hydrogen atom; R$^2$ is a lower alkenyloxy group; and R$^3$ and R$^4$ may form a 5- or 6-membered heterocyclic group together with the adjacent nitrogen atom, further with or without additional nitrogen atom, sulfur atom or oxygen atom; said heterocyclic group may have substituents selected from the group consisting of a lower alkyl group and a lower alkanoyl group.

20) A carbostyril derivative represented by the above-mentioned general formula (1) and salt thereof, wherein R$^1$ is a hydrogen atom; R$^2$ is a lower alkenyl group; and R$^3$ and R$^4$ may form, together with the adjacent nitrogen atom, further with or without additional nitrogen atom, sulfur atom or oxygen atom, a 5- or 6-membered heterocyclic group which may have substituents selected from the group consisting of a lower alkyl group and a lower alkanoyl group.

21) A carbostyril derivative represented by the above-mentioned general formula (1) and salt thereof, wherein R$^1$ is a lower alkyl group; R$^2$ is a hydrogen atom; and R$^3$ and R$^4$ may form, together with the adjacent nitrogen atom, further with or without additional nitrogen atom, sulfur atom or oxygen atom, a 5- or 6-membered heterocyclic group which may have substituents selected from the group consisting of a lower alkyl group and a lower alkanoyl group.

22) A carbostyril derivative represented by the above-mentioned general formula (1) and salt thereof, wherein R$^1$ and R$^2$ are lower alkyl groups; and R$^3$ and R$^4$ may form, together with the adjacent nitrogen atom, further with or without additional nitrogen atom, sulfur atom or oxygen atom, a 5- or 6-membered heterocyclic group which may have substituents selected from the group consisting of a lower alkyl group and a lower alkanoyl group.

23) A carbostyril derivative represented by the above-mentioned general formula (1) and salt thereof, wherein $R^1$ is a lower alkyl group; $R^2$ is a lower alkoxy group; and $R^3$ and $R^4$ may form, together with the adjacent nitrogen atom, further with or without additional nitrogen atom, sulfur atom or oxygen atom, a 5- or 6-membered heterocyclic group which may have substituents selected from the group consisting of a lower alkyl group and a lower alkanoyl group.

24) A carbostyril derivative represented by the above-mentioned general formula (1) and salt thereof, wherein $R^1$ is a lower alkyl group; $R^2$ is a lower alkenyloxy group; and $R^3$ and $R^4$ may form a 5- or 6-membered heterocyclic group together with the adjacent nitrogen atom, further with or without additional nitrogen atom, sulfur atom or oxygen atom; said heterocyclic group may have substituents selected from the group consisting of a lower alkyl group and a lower alkanoyl group.

25) A carbostyril derivative represented by the above-mentioned general formula (1) and salt thereof, wherein $R^1$ is a lower alkyl group; $R^2$ is a lower alkenyl group; and $R^3$ and $R^4$ may form, together with the adjacent nitrogen atom, further with or without additional nitrogen atom, sulfur atom or oxygen atom, a 5- or 6-membered heterocyclic group which may have substituents selected from the group consisting of a lower alkyl group and a lower alkanoyl group.

26) A carbostyril derivative represented by the above-mentioned general formula (1) and salt thereof, wherein $R^1$ is a lower alkenyl group; $R^2$ is a hydrogen atom; and $R^3$ and $R^4$ may form, together with the adjacent nitrogen atom, further with or without additional nitrogen atom, sulfur atom or oxygen atom, a 5- or 6-membered heterocyclic group which may have substituents selected from the group consisting of a lower alkyl group and a lower alkanoyl group.

27) A carbostyril derivative represented by the above-mentioned general formula (1) and salt thereof, wherein $R^1$ is a lower alkenyl group; $R^2$ is a lower alkyl group; and $R^3$ and $R^4$ may form, together with the adjacent nitrogen atom, further with or without additional nitrogen atom, sulfur atom or oxygen atom, a 5- or 6-membered heterocyclic group which may have substituents selected from the group consisting of a lower alkyl group and a lower alkanoyl group.

28) A carbostyril derivative represented by the above-mentioned general formula (1) and salt thereof, wherein $R^1$ is a lower alkenyl group; $R^2$ is a lower alkoxy group; and $R^3$ and $R^4$ may form, together with the adjacent nitrogen atom, further with or without additional nitrogen atom, sulfur atom or oxygen atom, a 5- or 6-membered heterocyclic group which may have substituents selected from the group consisting of a lower alkyl group and a lower alkanoyl group.

29) A carbostyril derivative represented by the above-mentioned general formula (1) and salt thereof, wherein $R^1$ is a lower alkenyl group; $R^2$ is a lower alkenyloxy group; and $R^3$ and $R^4$ may form, together with the adjacent nitrogen atom, further with or without additional nitrogen atom, sulfur atom or oxygen atom, a 5- or 6-membered heterocyclic group which may have substituents selected from the group consisting of a lower alkyl group and a lower alkanoyl group.

30) A carbostyril derivative represented by the above-mentioned general formula (1) and salt thereof, wherein $R^1$ and $R^2$ are lower alkenyl groups; and $R^3$ and $R^4$ may form, together with the adjacent nitrogen atom, further with or without additional nitrogen atom, sulfur atom or oxygen atom, a 5- or 6-membered heterocyclic group which may have substituents selected from the group consisting of a lower alkyl group and a lower alkanoyl group.

31) A carbostyril derivative represented by the above-mentioned general formula (1) and salt thereof, wherein $R^1$ is a hydrogen atom; $R^2$ is a tetrahydropyranyloxy group; and $R^3$ and $R^4$ are lower alkyl groups which may have hydroxyl group as the substituents.

32) A carbostyril derivative represented by the above-mentioned general formula (1) and salt thereof, wherein $R^1$ is a lower alkyl group; $R^2$ is a tetrahydropyranyloxy group; and $R^3$ and $R^4$ are lower alkyl groups which may have hydroxyl group as the substituents.

33) A carbostyril derivative represented by the above-mentioned general formula (1) and salt thereof, wherein $R^1$ is a lower alkenyl group; $R^2$ is a tetrahydropyranyloxy group; and $R^3$ and $R^4$ are lower alkyl groups which may have hydroxyl group as the substituents.

34) A carbostyril derivative represented by the above-mentioned general formula (1) and salt thereof, wherein $R^1$ is a hydrogen atom; $R^2$ is a tetrahydropyranyloxy group; and $R^3$ and $R^4$ may form, together with the adjacent nitrogen atom, further with or without additional nitrogen atom, sulfur atom or oxygen atom, a 5- or 6-membered heterocyclic group which may have substituents selected from the group consisting of a lower alkyl group and a lower alkanoyl group.

35) A carbostyril derivative represented by the above-mentioned general formula (1) and salt thereof, wherein $R^1$ is a lower alkyl group; $R^2$ is a tetrahydropyranyloxy group; and $R^3$ and $R^4$ may form, together with the adjacent nitrogen atom, further with or without additional nitrogen atom, sulfur atom or oxygen atom, a 5- or 6-membered heterocyclic group which may have substituents selected from the group consisting of a lower alkyl group and a lower alkanoyl group.

36) A carbostyril derivative represented by the above-mentioned general formula (1) and salt thereof, wherein $R^1$ is a lower alkenyl group; $R^2$ is a tetrahydropyranyloxy group; and $R^3$ and $R^4$ may form, together with the adjacent nitrogen atom, further with or without additional nitrogen atom, sulfur atom or oxygen atom, a 5- or 6-membered heterocyclic group which may have substituents selected from the group consisting of a lower alkyl group and a lower alkanoyl group.

The carbostyril derivatives of the present invention represented by the general formula (1) can be prepared by various processes, and among of these processes, typical methods can be exemplified as the following reaction formulae.

Reaction formula-1

$R^5O$—[quinolinone ring with $R^2$ substituent and $R^1$ on N]—(3) $\xrightarrow{R^3R^4NH \ (4) \ \text{or} \ (R^3R^4N)_2CH_2 \ (5)}$ -continued

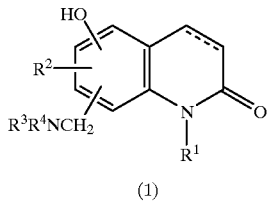

(wherein $R^1$, $R^2$, $R^3$, $R^4$ and the carbon—carbon bond between 3- and 4-positions in the carbostyril skeleton are the same as defined the above; $R^5$ is a hydrogen atom, a tetrahydropyranyl group or a lower alkanoyl group).

The reaction of a compound (3) with a compound (4) is carried out by reacting a compound (3), a compound (4) and formaldehyde in the presence or absence of an acid in a suitable solvent.

As to the solvent used in this reaction, any solvent used for Mannich reaction can be used, for example water; alcohols such as methanol, ethanol, isopropanol and the like; alkanoic acids such as acetic acid and propionic acid and the like; acid anhydrides such as acetic anhydride and the like; polar solvents such as acetone, dimethylformamide and the like; or mixtures of these solvents can be exemplified.

As to the acid used in this reaction, mineral acids such as hydrochloric acid, hydrobromic acid and the like, organic acid such as acetic acid can be exemplified.

As to the formaldehyde used in this reaction, an aqueous solution containing 20 to 40% of formaldehyde, trimer of formaldehyde, polymer of formaldehyde (paraformaldehyde) and the like can be suitably used.

A compound (4) may be used generally in an amount of at least an equimolar quantity, preferably an equimolar to 5 times the molar quantity to one molar quantity of a compound (3). Further, formaldehyde may be used in an amount of at least an equimolar quantity, generally a large excess quantity to one molar quantity of a compound (3). Generally, this reaction is carried out suitably at 0 to 200° C., preferably at room temperature to 150° C., and the reaction is generally finished in about 0.5 to 15 hours.

In case of using a compound (3), wherein $R^5$ is a tetrahydropyranyl group or a lower alkanoyl group, before adding formaldehyde to the reaction system, when $R^5$ is a lower alkanoyl group, then compound (3) is previously reacted with an excess amount of a compound (4) at 60 to 80° C. for 30 minutes to 2 hours; or when $R^5$ is a tetrahydropyranyl group, then compound (3) is reacted with an acid at 60 to 80° C. for 30 minutes to 2 hours; so as to introduce the compound (3) wherein corresponding $R^5$ is converted into a hydrogen atom. Then compound (3) wherein $R^5$ is a hydrogen atom is reacted under the reaction condition similar to the above-mentioned reaction of a compound (3) with a compound (4), by adding compound (4) and formaldehyde to the reaction system.

In case of using a compound (3) wherein $R^5$ is a tetrahydropyranyl group or a lower alkanoyl group, said compound (3) is subjected to hydrolysis to introduce to the corresponding compound (3) wherein $R^5$ is a hydrogen atom, then said compound (3) may be reacted with a compound (4). This hydrolysis is carried out in a suitable solvent or without solvent, and in the presence of an acid or basic compound. As to the solvent used in this hydrolysis, examples are water; lower alcohols such as methanol, ethanol, isopropanol and the like; ketones such as acetone, methyl ethyl ketone and the like; ethers such as diethyl ether, dioxane, tetrahydrofuran, ethylene glycol dimethyl ether and the like; fatty acids such as acetic acid, formic acid and the like; mixed solvents thereof can be exemplified. As to the acid used in this hydrolysis, mineral acids such as sulfuric acid, hydrochloric acid, hydrobromic acid and the like; organic acid such as formic acid, acetic acid, aromatic sulfonic acid and the like can be exemplified. As to the basic compound, metal carbonates such as sodium carbonate, potassium carbonate and the like; metal hydroxides such as sodium hydroxide, potassium hydroxide, calcium hydroxide and the like can be exemplified. This hydrolysis is carried out generally at about room temperature to 200° C., preferably carried out at about room temperature to 150° C., and is generally finished in about 10 minutes to 25 hours.

The reaction of a compound (3) with a compound (5) is carried out in the presence of an acid, and in a suitable solvent or without solvent. As to the acid used in this reaction, mineral acids such as sulfuric acid, hydrochloric acid, hydrobromic acid and the like; organic acids such as formic acid, acetic acid, acetic anhydride and the like can be exemplified. Among these acids, acetic anhydride is used preferably. As to the solvent, any one of the solvent used in the reaction of a compound (3) with a compound (4) can also be used. The amount of a compound (5) is used at least an equimolar quantity, preferably an equimolar to 5 times the molar quantity thereof may be used to one molar quantity of a compound (3). This reaction is carried out generally at 0 to 150° C., preferably proceeds at room temperature to about 100° C., and is finished generally within about 0.5 to 5 hours.

Reaction formula-2

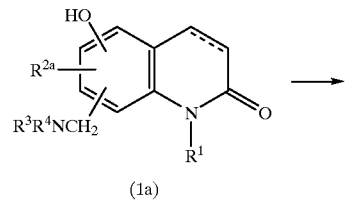

(1a)

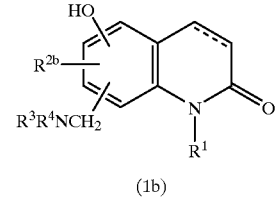

(1b)

(wherein $R^1$, $R^3$, $R^4$ and the carbon—carbon bond between 3- and 4-positions in the carbostyril skeleton are the same as defined the above; $R^{2a}$ is a lower alkenyl group or a lower alkenyloxy group; $R^{2b}$ is a lower alkyl group or a lower alkoxy group).

Conversion of a compound (1a) to a compound (1b) is carried out in a suitable solvent by a catalytic hydrogenation. As to the solvent used in this catalytic reduction, examples are water; acetic acid; alcohols such as methanol, ethanol, isopropanol and the like; hydrocarbons such as hexane, cyclohexane and the like; ethers such as dioxane, tetrahydrofuran, diethyl ether, diethylene glycol dimethyl ether and the like; esters such as ethyl acetate, methyl acetate and the like; aprotic polar solvents such as N,N-dimethylformamide; and mixed solvents thereof can be exemplified. As to the catalysts for the catalytic hydrogenation, examples are palladium, palladium-black, palladium-carbon, platinum, platinum oxide, cupper chromite, Raney nickel and the like can be exemplified.

Such catalyst may be used generally in an amount of 0.02 to 1 part per 1 part of the starting material. In carrying out of this reaction, an acid such as hydrochloric acid may be added in the reaction system. The reaction temperature may be generally at about −20 to 150° C., preferably as 0 to 100° C., and the hydrogen gas pressure may be generally at 1 to 10 atmospheric pressure, and the reaction is generally finished in about 0.5 to 10 hours.

The compound (3) which is used as the starting material in the above-mentioned Reaction formula-1 is prepared, for example, by the following Reaction formula-3 and Reaction formula-4.

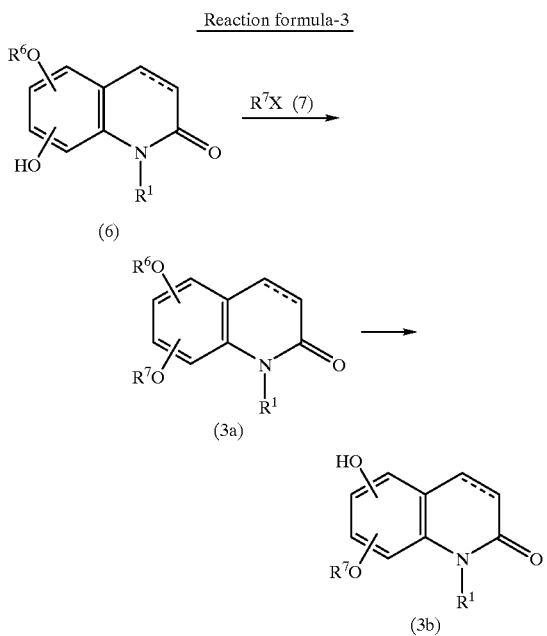

(wherein $R^1$ and the carbon—carbon bond between 3- and 4-positions in the carbostyril skeleton are the same as defined above; $R^6$ is a lower alkanoyl group or tetrahydropyranyl group; $R^7$ is a lower alkyl group or a lower alkenyl group; and X is a halogen atom).

The reaction of a compound (6) with a compound (7) is carried out generally in a suitable inert solvent, and in the presence of or absence of a basic compound. As to the inert solvent used in this reaction, examples are aromatic hydrocarbons such as benzene, toluene, xylene and the like; ethers such as tetrahydrofuran, dioxane, diethyelene glycol dimethyl ether and the like; halogenated hydrocarbons such as dichloromethane, chloroform, carbon tetrachloride and the like; lower alcohols such as methanol, ethanol, isopropanol, butanol, tert-butanol and the like; acetic acid, ethyl acetate, acetone, acetonitrile, pyridine, dimethyl sulfoxide, dimethylformamide, hexamethylphosphoryl triamide and the like; and mixed solvents thereof. As to the basic compound, examples are metal carbonates such as sodium carbonate, potassium carbonate, sodium hydrogencarbonate, potassium hydrogencarbonate and the like; metal hydroxide such as sodium hydroxide, potassium hydroxide; sodium hydride, metallic potassium, metallic sodium, sodium amide; metal alcoholates such as sodium methylate, sodium ethylate and the like; organic basic compounds such as pyridine, N-ethyl-diisopropylamine, dimethylaminopyridine, triethylamine, 1,5-diazabicyclo[4.3.0]non-5-ene (DBN), 1,8-diazabicyclo[5.4.0]undec-7-ene (DBU), 1,4-diazabicyclo-[2.2.2]octane (DABCO) and the like can be exemplified.

The ratio of amount of a compound (6) to amount of a compound (7) is not specifically restricted and it may be selected from a wide range, thus at least an equimolar quantity, preferably an equimolar to about 10 times the molar quantity of the latter may be used to the former. This reaction is carried out generally at 0 to about 200° C., preferably 0 to about 170° C., and is generally finished in about 30 minutes to 30 hours. Into this reaction system, a metal iodide such as sodium iodide, potassium iodide and the like may be added.

The reaction for introducing a compound (3a) to a compound (3b) is carried out under the condition similar to the hydrolysis of a compound (3) wherein $R^5$ is a tetrahydropyranyl group or a lower alkanoyl group.

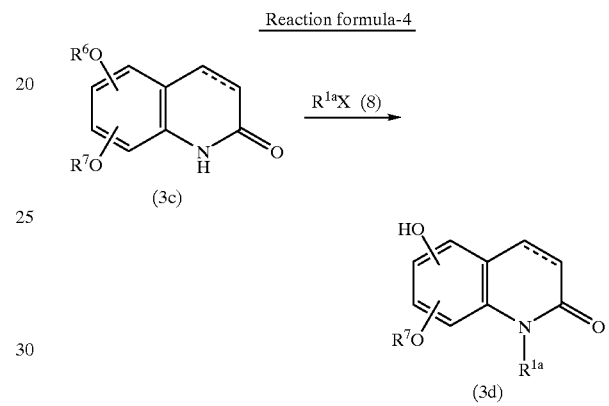

(wherein $R^6$, $R^7$, X and the carbon—carbon bond between 3- and 4-positions in the carbostyril skeleton are the same as defined in the above; and $R^{1a}$ is a lower alkyl group or a lower alkenyl group).

The reaction of a compound (3c) with a compound (8) is carried out, for example in the presence of a basic compound and in a suitable solvent. As to the basic compound, sodium hydride, metallic potassium, metallic sodium, sodium amide, potassium amide and the like can be exemplified. As to the solvent, ethers such as dioxane, diethylene glycol dimethyl ether and the like can be exemplified; aromatic hydrocarbons such as toluene, xylene and the like; dimethylformamide, dimethyl sulfoxide, hexamethylphosphoryl triamide and the like can be exemplified. The ratio of amount of a compound (3c) to amount of a compound (8) is not specifically restricted and it can be selected from a wide range, and generally at least an equimolar quantity, preferably an equimolar to 2 times the molar quantity of the latter may be used to the former. This reaction is carried out generally at 0 to about 70° C., preferably at 0° C. to about room temperature, and the reaction is finished generally in 0.5 to about 12 hours.

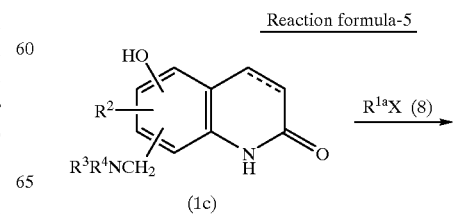

-continued

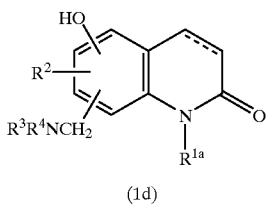

(1d)

(wherein $R^{1a}$, $R^2$, $R^3$, $R^4$, X and the carbon—carbon bond between 3- and 4-positions in the carbostyril skeleton are the same as defined in the above).

The reaction of a compound (1c) with a compound (8) is carried out under the condition similar to that of employed in the reaction of a compound (3c) with a compound (8) in the above-mentioned Reaction formula-4.

Reaction formula-6

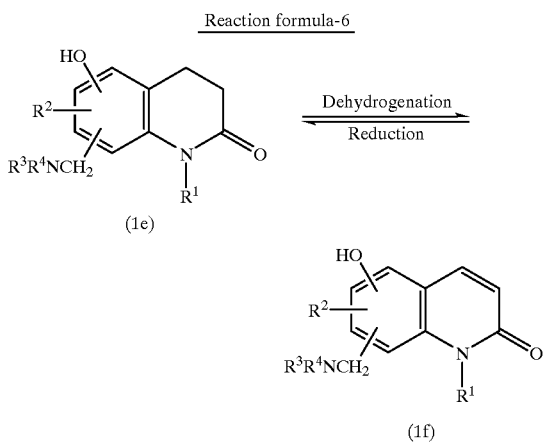

(wherein $R^1$, $R^2$, $R^3$ and $R^4$ are the same as defined in the above).

The dehydrogenation of a compound (1e) is carried out in a suitable solvent by using an oxidizing agent. As to the oxidizing agent, benzoquinones such as 2,3-dichloro-5,6-dicyanobenzoquinone, chloranil (2,3,5,6-tetrachlorobenzoquinone) and the like; halogenating agents such as N-bromosuccinimide, N-chlorosuccinimide, bromine and the like; and dehydrogenating catalyst such as selenium dioxide, palladium-carbon, palladium-black, palladium oxide, Raney nickel and the like can be exemplified. Used amount of the halogenating agent is not specifically restricted and can be selected from a wide range, and generally 1 to 5 times the molar quantity, preferably 1 to 2 times the molar quantity of the halogenating agent may be used to the starting material. Further when the dehydrogenating catalyst is used, generally an excess amount of the catalyst may be used. As to the solvent, ethers such as dioxane, tetrahydrofuran, methoxymethanol, dimethoxyethane and the like; aromatic hydrocarbons such as benzene, toluene, xylene, cumene and the like; halogenated hydrocarbons such as dichloromethane, dichloroethane, chloroform, carbon tetrachloride and the like; alcohols such as butanol, amyl alcohol, hexanol and the like; polar protic solvents such as acetic acid; and polar aprotic solvents such as dimethylformamide, dimethyl sulfoxide, hexamethylphosphoryl triamide and the like can be exemplified. This reaction is carried out generally at room temperature to about 300° C., preferably at room temperature to about 200° C., and is completed generally in 1 to 40 hours.

For this reducing reaction of a compound (f), the reaction conditions of a common catalytic reduction can be widely applied. As to the catalyst, metallic catalyst such as palladium, palladium-carbon, platinum, Raney nickel and the like can be exemplified. These metallic catalysts are used in general catalytic amount. As to the solvent, water; alcohols such as methanol, ethanol, isopropanol, and the like; ethers such as dioxane, tetrahydrofuran and the like; aliphatic hydrocarbons such as hexane, cyclohexane and the like; esters such as ethyl acetate and the like; and mixtures of these solvents can be exemplified. Said reducing reaction can be carried out either at an atmospheric pressure or under a pressurized condition, and generally may be carried out at an atmospheric pressure to about 20 kg/cm$^2$, preferably at an atmospheric pressure to about 10 kg/cm$^2$. The reaction may be carried out generally at temperature of about 0 to 150° C., preferably at about room temperature to 100° C.

Among carbostyril derivatives represented by the general formula (1) according to the present invention, wherein a compound having acidic group can be converted into salt thereof by reacting it with a pharmaceutically acceptable basic compound. As to such basic compound, metal hydroxides such as sodium hydroxide, potassium hydroxide, lithium hydroxide, calcium hydroxide and the like; alkali metal carbonates or bicarbonates such as sodium carbonate, sodium hydrogencarbonate and the like; alkali metal alcoholates such as sodium methylate, potassium ethylate and the like can be exemplified.

Further, among carbostyril derivatives represented by the general formula (1) according to the present invention, wherein a compound having basic group can be converted into salt thereof easily by reacting it with a pharmaceutically acceptable acid. As to such acid, inorganic acids such as sulfuric acid, nitric acid, hydrochloric acid, hydrobromic acid and the like: organic acids such as acetic acid, p-toluenesulfonic acid, ethanesulfonic acid, oxalic acid, maleic acid, citric acid, succinic acid, benzoic acid and the like can be exemplified.

Additionally, the above-mentioned carbostyril derivatives represented by the general formula (1) involve stereo isomers and optical isomers.

The desired carbostyril derivatives prepared by the above-mentioned Reaction formulas can be isolated from the reaction systems by common separation methods and can be further purified, for example by distillation method, recrystallization method, column chromatography, ion-exchange chromatography, gel chromatography, affinity chromatography, preparative thin-layer chromatography, solvent extraction method and the like can be applied.

Thus obtained carbostyril derivatives of the present invention are used in the form of general types of pharmaceutical compositions. Such pharmaceutical compositions are prepared by formulating with commonly used diluents such as fillers, bulking agents, binders, wetting agents, disintegrators, surface active agents, lubricants and the like, or excipients. Various forms of pharmaceutical compositions can be selected depend on the purpose for treating, and typical forms of the compositions including tablets, pills, powders, liquids, suspensions, emulsions, granules, capsules, suppositories, injections (solutions and suspensions) and the like, and pharmaceutical compositions for external uses such as inhalants, nebulizing agents such as aerosol preparations for external use, further liquid paint preparations, lotions, gels, oily ointments, emulsion type ointment basis such as O/W type hydrophylic ointments, and W/o type water absorbing ointments, water soluble ointment basis, creams, liniments, cataplasms, pastes, plasters, emulsions and the like, and sheet-form preparations can be exemplified.

For the purpose of shaping the pharmaceutical composition in the form of tablets, carriers which are known in this field can be used, for example excipients such as lactose, white sugar, sodium chloride, glucose, urea, starch, calcium carbonate, kaolin, crystalline cellulose, silicic acid and the like; binding agents such as water, ethanol, propanol, simple syrup, glucose solution, starch solution, gelatin solution, carboxymethyl-cellulose, shelac, methylcellulose, calcium phosphate, polyvinylpyrrolidone and the like; disintegrators such as dried starch, sodium alginate, agar—agar powder, laminalia powder, sodium hydrogencarbonate, calcium carbonate, esters of polyoxyethylenesorbitan fatty acid, sodium laurylsulfate, monoglyceride of stearic acid, starch, lactose and the like; disintegration inhibitors such as white sugar, stearin, cacao butter, hydrogenated oils and the like; absorption accelarators such as quarternary ammonium base, sodium laurylsulfate and the like; wetting agents such as glycerin, starch and the like; adsorbing agents such as starch, lactose, kaolin, bentonite, colloidal silicic acid and the like; and lubricants such as refined talc, stearic acid, boric acid powder, polyethylene glycols and the like can be used. Further, the tablets can be coated with common coating materials to make them as sugar coated tablets, gelatin film coated tablets, tablets coated with enteric coatings, tablets coated with films or double layered tablets and multi-layered tablets.

For the purpose of shaping the pharmaceutical composition in the form of pills, carriers which are known and widely used in this field can be used, for example, excipients such as glucose, lactose, starch, coconut butter, hydrogenated oils, kaolin, talc and the like; binders such as powdered gum arabic, powdered Tragacanth, gelatin, ethanol and the like; disintegrators; such as laminalia, agar—agar are included.

For the purpose of shaping the pharmaceutical composition in the form of suppositories, carriers which are known and widely used in this field can be used, for example, polyethylene glycols, coconut butter, higher alcohols, esters of higher alcohols, gelatin and semi-synthesized glycerides are included.

For the purpose of shaping the pharmaceutical composition in the form of capsules, generally, the effective ingredient is mixed with the above-mentioned various carriers, then the mixture thus obtained is filled in hard capsules or soft capsules.

For the purpose of shaping the pharmaceutical composition in the form of injection preparations, a solution, an emulsion or a suspension of the effective ingredient is sterilized and is preferably made it isotonic to the blood. In making an injection preparation, whatever carriers which are commonly used in this field can be applied. For example, water, ethyl alcohol, ethylene glycols, propylene glycols, ethoxylated isostearyl alcohol, polyoxylated isostearyl alcohol, polyoxyethylenesorbitane fatty acid esters can be used. In these instances, adequate amounts of sodium chloride, glucose or glycerin can be added to contain in the desired injection preparation for the purpose of having them isotonic. Furthermore, common dissolving agents, buffering agents, analgesic agents may be added. If necessary, coloring agents, preservatives, purfumes, seasoning agents, sweetening agents and other medicines can be added into the desired preparations.

The amount of a compound of the general formula (1) and salt thereof to be contained in the pharmaceutical preparations of the present invention is not specifically restricted and can be selected from a wide range, generally 1 to 70% by weight of the compound may be contained in the whole composition.

Administration method of the pharmaceutical preparation of the present invention is not specifically restricted, thus it is administered by various methods depend on the type of administration form, the age of the patient, the distinction of sex, the condition of the symptoms and other factors. For example, tablets, pills, solutions, suspensions, emulsions, granules and capsules are administered orally. Injection preparations are administered intravenously singly or mixed with common injection transfusions, such as glucose solutions and amino acids solutions. If necessary, the injection preparations are administered singly intramuscularly, intracutaneously, subcutaneously or intraperitoneally. Suppositories are administered into the rectum. External preparations are administered by coating on the skin.

In case of using the carbostyril derivatives of the present invention as to ingredients of cosmetics, they can be used in creams, lotions and oils for suntan or for protecting sunburn. In addition to the above, generally they are added as for UV-protecting agents and UV-inhibitors, or suntan agents and sunburn protecting agents.

Concretely, cosmetics can be exemplified such as face powder, cream, milk lotion, lotion, toilet water, toilet oil, bleaching agent and the like.

As to the forms of these cosmetics, liquid, oil, lotion, liniment, oily ointment base, emulsion-type ointment base such as O/W-type hydrophilic ointment base and W/O-type water absorbing ointment base, water-soluble ointment base, paste, plaster, patch, cream, milk lotion and the like can be exemplified. These forms of cosmetics can be prepared by common and widely known methods of preparation.

For example, as to the ointment base, at least one oleaginous base can be used singly, or mixture of two or more of them can be used; or at least one water-soluble ointment base can be used singly, or mixture of two or more of them can be used.

Specific examples of these ointment base are fats and oils such as peanut oil, sesame oil, soybean oil, safflower oil, avocado oil, sunflower oil, corn oil, rapeseed oil, cotton seed oil, castor oil, camellia oil, coconut oil, olive oil, poppy seed oil, cacao butter, beef tallow, lard, wool fat and the like; modified bases obtained by subjecting these fats and oils to chemical changes such as hydrogenation; mineral oils such as petrolatum, paraffin, silicone oil, squalane and the like; higher fatty acid esters of isopropyl myristate, n-butyl myristate, isopropyl linoleate, propyl ricinolate, isopropyl ricinolate, isobutyl ricinoleate, heptyl ricinolate, diethyl sebacate, diisopropyl adipate; higher aliphatic alcohols such as cetyl alcohol and stearyl alcohol; and waxes such as bleached bees wax, spermaceti, Japan wax, lanolin, carnauba wax, shellac wax and the like; higher fatty acids such as stearic acid, oleic acid, palmitic acid and the like; mixtures of mono-, di- and tri-glycerides of saturated or unsaturated fatty acids having 12 to 18 carbon atoms; polyhydric alcohols such as ethylene glycol, polyethylene glycols, propylene glycols, polypropylene glycols, glycerin, batyl alcohol, pentaerythritol, sorbitol, mannitol and the like; gummy substances such as arabic gum, benzoin gum, guaiacum, tragacanth gum and the like; water-soluble natural high polymers such as gelatin, starch, casein, dextrin, pectin, sodium pectate, sodium alginate, methyl cellulose, ethyl cellulose, carboxymethyl cellulose, hydroxyethyl cellulose, hydroxypropyl cellulose, nitrocellulose, crystalline cellulose and the like; water-soluble synthetic high polymers such as polyvinyl alcohols, poly(vinyl methyl ether), polyvinylpyrrolidone, sodium polyacrylate, carboxyvinyl polymer, polyethyleneimine and the like; non-ionic, anionic, amphoteric and cationic surface active agents; ethanol, isopropanol and water and the like can be exemplified.

In case of preparing the above-mentioned cosmetics, various types of the above-mentioned cosmetic bases, for example excipients, binders, lubricants, disintegrators and the like can be used. Further, if necessary, various kinds of ingredients and additives for example, oily materials such as various kinds of fats and oils, waxes, hydrocarbons, fatty acids, higher alcohols, ester oils, metallic soaps and the like; pharmacologically effective agents such as animal and vegetable extracts, vitamins, hormones, amino acids and the like can be used by suitably combined thereof. Thus obtained cosmetics can be used by diluted further with water olive oil or a suitable solvent.

The amount of the carbostyril derivatives of the general formula (1) or salts thereof to be contained in the cosmetics of the present invention is not specifically restricted and can be selected from a wide range, and the amount may be generally selected within the range of 0.1 to 50% by weight in the whole composition.

The amount of using the pharmaceutical preparation or cosmetics of the present invention containing the carbostyril derivative of the general formula (1) of the present invention as the effective ingredient is suitably selected depend on the administration method, the age of the patient, the distinction of sex and related other conditions, the degree of disease condition of the patient. In case of using as pharmaceutical preparation, the amount the effective ingredient may be administered about 0.6 to 50 mg per 1 kg of the body weight per day, and in case of using as cosmetics, the amount of the effective ingredient may be administered about 0.1 to 30 mg per 1 kg of the body weight per day. These pharmaceutical preparation or cosmetics can be divided for administration purpose in 2 to 4 times a day.

EXAMPLES

The present invention will be explained in more detail by illustrating Reference examples, Examples and Pharmacological tests as follows.

Reference example 1

65 Grams of 5-acetoxy-3,4-dihydro-8-hydroxy-2(1H)-quinolinone was dissolved in 500 ml of dimethylformamide (DMF), to this solution were added 52 g of potassium carbonate powder and 50 ml of allyl bromide, the mixture thus obtained was stirred at room temperature for 8 hours. To this reaction mixture was diluted with 500 ml of water, extracted with 2 liter of ethyl acetate. The extract was washed with water, dried over anhydrous magnesium sulfate, then concentrated to dryness under reduced pressure. The residue was recrystallized from ethanol, there was obtained 70 g of 5-acetoxy-8-allyloxy-3,4-dihydro-2(1H)-quinolinone as brown needle-like crystals.

Melting point: 137–139° C.

Reference example 2

9 Grams of 5-acetoxy-8-allyloxy-3,4-dihydro-2(1H)-quinolinone was dissolved in 100 ml of DMF, 1.51 g of 60%-sodium hydride was added gradually in limited amounts to this solution, this reaction mixture was stirred at room temperature until generation of hydrogen gas ceased. Under stirring and ice-cooling conditions, 100 ml of water was added to this reaction mixture, extracted with ethyl acetate. The extract was washed with water, dried over anhydrous magnesium sulfate, the dried extract was concentrated under reduced pressure. The oily product thus obtained was purified by a silica gel column chromatography, there was obtained 7 g of 5-acetoxy-8-allyloxy-3,4-dihydro-1-methyl-2(1H)-quinolinone as pale yellow oily product.

$^1$H-NMR (CDCl$_3$) δ ppm: 2.30 (3H, s), 2.52 (2H, dd), 2.65 (2H, dd), 3.40 (3H, s), 4.51–4.55 (2H, m), 5.29 (1H, dd), 5.39 (1H, dd), 5.96–6.11 (1H, m), 6.76 (1H, d), 6.80 (1H, d).

Reference example 3

6 Grams of 5-hydroxy-3,4-dihydro-8-allyloxy-2(1H)-quinolinone was dissolved in 20 ml of dihydropyran, to this solution was added 2 ml of concentrated hydrochloric acid, then refluxed by heating for 1 hour. To this reaction mixture was added 5 g of potassium carbonate powder and stirred, then concentrated under reduced pressure. The residue thus obtained was extracted with ethyl acetate, the extract was washed with water, dried over anhydrous magnesium sulfate, again concentrated under reduced pressure to obtained pale yellow oily product. A mixed solvent of ethyl acetate-n-hexane was added to the oily product and allowed to stand for crystallization. There was obtained 8 g of 5-tetrahydropyranyloxy-8-allyloxy-3,4-dihydro-2(1H)-quinolinone as white amorphous product.

Melting point: 111–113° C.

Reference example 4

7 Grams of 5-tetrahydropyranyloxy-8-allyloxy-3,4-dihydro-2(1H)-quinolinone was dissolved in 50 ml of DMF, then 1 g of 60%-sodium hydride was added gradually in limited amounts to this solution, the reaction mixture was stirred at room temperature until generation of hydrogen gas ceased. To this reaction mixture was added 2.7 g of prenyl chloride, stirred at room temperature for 8 hours. To this mixture was added 100 ml of water and stirred, the mixture was acidified by adding concentrated hydrochloric acid, stirred at 60° C. for 1 hour to remove the tetrahydropyranyl group at 5-position. The mixture was extracted with ethyl acetate, and washed with water, dried over anhydrous magnesium sulfate, then concentrated under reduced pressure. The oily product thus obtained was purified by a silica gel column chromatography, there was obtained 4.2 g of 5-hydroxy-8-allyloxy-3,4-dihydro-1-prenyl-2(1H)-quinolinone as pale yellow oily product.

$^1$H-NMR (CDCl$_3$) δ ppm: 1.60 (6H, s), 2.52 (2H, dd), 2.80 (2H, dd), 4.42–4.62 (2H, m), 5.13 (1H, t), 5.24 (1H, dd), 5.35 (1H, dd), 5.96–6.11 (1H, m), 6.80 (1H, d), 6.69 (1H, d).

Reference example 5

10 Grams of 5-acetoxy-8-hydroxy-2(1H)-quinolinone was dissolved in 100 ml of DMF, to this solution was added 14 g of potassium carbonate and 9 ml of allyl bromide, stirred at room temperature for 8 hours. Under ice-cooling and stirring conditions, the reaction mixture was acidified by adding hydrochloric acid, this mixture was diluted by adding 200 ml of water. The mixture was extracted with 500 ml of ethyl acetate, the extract was washed with water, dried over anhydrous magnesium sulfate, then concentrated to dryness under reduced pressure. The residue thus obtained was recrystallized from a mixed solvent of ethyl acetate-n-hexane, there was obtained 9.8 g of 5-acetoxy-8-allyloxy-2(1H)-quinolinone as pale yellow needle-like crystals.

Melting point: 142–143° C.

Reference example 6

9.16 Grams of 5-acetoxy-8-tetrahydropyranyloxy- 3,4-dihydro-2(1H)-quinolinone was dissolved in 200 ml of methanol, to this solution was added 45 ml of an aqueous solution of 10%-potassium carbonate, refluxed by heating for 1 hour, then concentrated to dryness under reduced pressure, there was obtained 5-hydroxy-8-tetrahydropyranyloxy-3,4-dihydro-2(1H)-quinolinone. This product was suspended in 100 ml of DMF, further 4.1 g of potassium carbonate was added to this suspension and stirred. To this mixture was added 3 ml of allyl bromide at room temperature and stirred for 8 hours. To this reaction mixture was added 200 ml of water, and extracted with ethyl acetate. The extract was washed with water, dried over anhydrous magnesium sulfate, concentrated under reduced pressure. The residue was recrystallized from ethyl acetate-n-hexane, there was obtained 6 g of 8-tetrahydropyranyloxy-5-allyloxy-3,4-dihydro-2(1H)-quinolinone as white solid product.

Melting point: 113–115° C.

Example 1

1.5 Grams of 5-acetoxy-3,4-dihydro-8-methoxy-2(1H)-quinolinone was suspended in 10 ml of ethanol, to this suspension were added 4 ml of 50%-dimethylamine aqueous solution and 2 ml of 37%-formalin, this mixture was refluxed by heating for 10 hours. The reaction mixture was concentrated to dryness under reduced pressure, the residue was purified by a silica gel flash column chromatography (eluent: methylene chloride: methanol=20:1→10:1). The oily product thus obtained was dissolved in ethanol, this solution was acidified by adding hydrochloric acid, concentrated to dryness, and recrystallized from ethanol, there was obtained 3.8 g of 6-(dimethylaminomethyl)-3,4-dihydro-5-hydroxy-8-methoxy-2(1H)-quinolinone hydrochloride as white powdery product.

Melting point: 210–212° C. (decomposed)

$^1$H-NMR (DMSO-$d_6$) δ ppm: 2.42 (2H, t), 2.70 (6H, s), 2.88 (2H, t), 3.76 (3H, s), 4.22 (2H, s), 7.07 (1H, s), 8.89 (1H, s), 9.12 (1H, s), 10.20 (1H, s).

Example 2

16.7 Grams of 5-hydroxy-3,4-dihydrocarbostyril was suspended in 300 ml of water, 20 ml of diethylamine was added thereto and stirred. To this mixture were added 20 ml of an aqueous solution of 37%-formalin, and stirred at room temperature for 2 hours. Precipitated crystals were collected by filtration, washed with water and dried. Recrystallized from ethanol, there was obtained 18 g of needle-like crystals, which was determined as 6-diethylaminomethyl-5-hydroxy-3,4-dihydrocarbostyril by means of an X-ray crystal structure analysis.

Melting point: 161–162° C.

$^1$H-NMR (CDCl$_3$) δ ppm: 1.61 (6H, t), 2.58–2.65 (6H, m), 2.93 (2H, t), 3.73 (2H, s), 6.23 (1H, d), 6.75 (1H, d), 8.44 (1H, s).

Example 3

16.3 Grams of 6-hydroxy-2(1H)-quinolinone was suspended in 300 ml of ethanol, under stirring 14.4 g of pyrrolidine and 20 ml of 37%-formalin were added to this suspension, this mixture was refluxed by heating for 12 hours. Precipitated crystals were filtered, washed with cold ethanol and dried. The dried crystals were dissolved in ethanol and the ethanol solution was acidified with hydrochloric acid, concentrated to dryness under reduced pressure. Recrystallized from water, there was obtained 13 g of 6-hydroxy-5-(1-pyrrolidinyl)methyl-2(1H)-quinolinone hydrochloride as pale yellow needle-like crystals.

Melting point: 242–243° C.

$^1$H-NMR (DMSO-$d_6$) δ ppm: 1.8–2.02 (4H, m), 3.10–3.30 (2H, m), 3.43 (4H, br.s), 4.60 (2H, d), 6.54 (1H, d), 7.32 (2H, s), 8.29 (1H, d), 10.12 (1H, br.s).

Example 4

5.2 Grams of 8-allyloxy-5-acetoxy-3,4-dihydro-2(1H)-quinolinone was dissolved in 20 ml of ethanol, under stirring, to this solution were added 10 ml of 50%-dimethylamine aqueous solution and 10 ml of 37%-formalin solution, this mixture was stirred at 70° C. for 8 hours. After cooled, the reaction mixture was concentrated to dryness, extracted with ethyl acetate, and the extract was washed with water and concentrated to dryness, the residue was purified by a silica gel column chromatography (eluent: methylene chloride: methanol=20:1→10:1). The crude crystals were dissolved in ethanol, and acidified with hydrochloric acid then concentrated to dryness. The residue was recrystallized from ethanol, there was obtained 3.8 g of 8-allyloxy-3,4-dihydro-5-hydroxy-6-dimethyl-aminomethyl-2(1H)-quinolinone hydrochloride as white powdery product.

Melting point: 184–186° C. (decomposed).

$^1$H-NMR (DMSO-$d_6$) δ ppm: 2.43 (2H, t), 2.69 (6H, s), 2.83 (2H, t), 4.20 (2H, s), 4.53 (2H, d), 5.24 (1H, dd), 5.43 (1H, dd), 5.96–6.11 (1H, m), 7.11 (1H, s), 8.94 (1H, s), 9.06 (1H, s), 10.18 (1H, br).

Example 5

41 Grams of 8-allyloxy-3,4-dihydro-5-hydroxy-2(1H)-quinolinone was dissolved in 500 ml of ethanol, under stirring 30 ml of piperidine and 30 ml of 37%-formalin were added to this solution, this mixture was stirred at 70° C. for 4 hours. After cooled, the reaction mixture was concentrated to dryness, extracted with 1 liter of methylene chloride, the extract was washed with water and dried, again concentrated to dryness. The residue was purified by a silica gel column chromatography (eluent: methylene chloride: ethyl acetate=20:1). The purified product was recrystallized from ethyl acetate, there was obtained 61g of 8-allyloxy-3,4-dihydro-5-hydroxy-6-(1-piperidinyl)methyl-2(1H)-quinolinone.

Melting point: 144–145° C.

Example 6

61 Grams of 8-allyloxy-3,4-dihydro-5-hydroxy-6-(1-piperidinyl)methyl-2(1H)-quinolinone was suspended in 50% ethanol aqueous solution, the suspension was acidified by adding a concentrated hydrochloric acid, then crystals were precipitated immediately. Allowed to stand for a while, the crystals precipitated were collected by filtration, washed with ice-cooled ethanol and dried. The dried crystals were recrystallized from ethanol, there was obtained 40 g of 8-allyloxy-3,4-dihydro-5-hydroxy-6-(1-piperidinyl)methyl-2(1H)-quinolinone hydrochloride as pale yellow needle-like crystals.

Melting point: 216–220° C. (decomposed).

$^1$H-NMR (DMSO-$d_6$) δ ppm: 1.12–1.95 (6H, m), 2.43 (2H, t), 2.75–3.00 (4H, br), 3.27 (2H, br), 4.17 (2H, s), 4.56 (2H, d), 5.24 (1H, dd), 5.44 (1H, dd), 6.02–6.17 (1H, m), 7.15 (1H, s), 8.85 (1H, s), 9.03 (1H, s), 10.18 (1H, br).

Example 7

5 Grams of 8-allyloxy-3,4-dihydro-5-hydroxy-6-(1-piperidinyl)methyl-2(1H)-quinolinone hydrochloride which was obtained in Example 6, was dissolved in 200 ml of ethanol, to this solution was added 200 mg of 5%-palladium-carbon, and carried out reduction at 3 kg/cm² of hydrogen pressure at room temperature. The catalyst was removed by filtration, and the filtrate was concentrated to dryness.

Residue thus obtained was recrystallized from ethanol, there was obtained 2.8 g of 3,4-dihydro-8-propyloxy-5-hydroxy-6-(1-piperidinyl)methyl-2(1H)-quinolinone hydrochloride as a white powder.

Melting point: 221–224° C. (decomposed).

$^1$H-NMR (DMSO-$d_6$) δ ppm: 0.99 (3H, t), 1.25–1.90 (8H, m), 2.43 (2H, t), 2.80–3.01 (4H, m), 3.85–4.00 (6H, m), 4.17 (2H, d), 5.24 (1H, dd), 5.35 (1H, dd), 5.96–6.11 (1H, m), 7.11 (1H, s), 8.82 (1H, s), 8.97 (1H, S), 10.21 (1H, S).

Example 8

8-Tetrahydropyranyloxy-5-allyloxy-3,4-dihydro-2(1H)-quinolinone which was obtained in Reference example 6, piperidine and 37%-formalin were reacted similarly as in Example 5, there was obtained 5-allyloxy-3,4-dihydro-8-hydroxy-7-(1-piperidinyl)methyl-2(1H)-quinolinone. Next, this compound was treated similarly as in Example 6 and recrystallized from ethanol, there was obtained 5-allyloxy-3,4-dihydro-8-hydroxy-7-(1-piperidinyl)methyl-2(1H) quinolinone hydrochloride as a white powder.

Melting point: 181–186° C. (decomposed).

$^1$H-NMR (DMSO-$d_6$) δ ppm: 1.30–1.85 (6H, m), 2.43 (2H, t), 2.80–3.00 (4H, m), 3.34 (2H, br), 4.19 (2H, s), 4.54 (2H, d), 5.27 (1H, dd), 5.43 (1H, dd), 6.05–6.20 (1H, m), 6.85 (1H, s), 8.91 (1H, s), 9.29 (1H, s), 9.90 (1H, br).

Examples 9–47

By using suitable starting materials and procedures similar to those employed in Examples 1–5 and 8, there were obtained compounds of Examples 9–47 shown in Tables 1–10 as follows.

TABLE 1

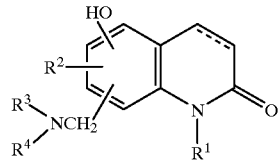

Compound of Example 9

$R^1$: H   $R^2$: —$CH_3$ (8-position)   $R^3$: —$C_2H_5$   $R^4$: —$C_2H_5$
OH: at 5-position
—$CH_2NR^3R^4$: at 6-position
Bond between 3- and 4-positions: Single bond
Crystal form: Colorless granular
Recrystallization solvent: Ethyl acetate NMR (1)
Melting point: 146–147° C.
Form: Free base Compound of Example 10

$R^1$: H   $R^2$: —$CH_3$ (6-position)   $R^3$: —$C_2H_5$   $R^4$: —$C_2H_5$
OH: at 5-position
—$CH_2NR^3R^4$: at 8-position
Bond between 3- and 4-positions: Single bond
Crystal form: White powder
Recrystallization solvent: Ethyl acetate NMR (2)
Melting point: 133–134° C.
Form: Free base

TABLE 2

Compound of Example 11

$R^1$: H   $R^2$: —$CH_3$ (8-position)   $R^3$: —$CH_3$   $R^4$: —$CH_3$
OH: at 5-position
—$CH_2NR^3R^4$: at 6-position
Bond between 3- and 4-positions: Double bond
Crystal form: Colorless needle-like
Recrystallization solvent: Ethanol   NMR (3)
Melting point: 196–206° C.   Form: Free base Compound of Example 12

$R^1$: H   $R^2$: —$CH_3$ (8-position)   $R^3$: —$CH_3$   $R^4$: —$CH_3$
OH: at 5-position
—$CH_2NR^3R^4$: at 6-position
Bond between 3- and 4-positions: Single bond
Crystal form: White powder
Recrystallization solvent: Ethanol
Melting point: 217–219° C.   Form: HCl salt Compound of Example 13

$R^1$: H   $R^2$: H   $R^3$: —$C_2H_5$   $R^4$: —$C_2H_5$
OH: at 5-position
—$CH_2NR^3R^4$: at 6-position
Bond between 3- and 4-positions: Single bond
Crystal form: Colorless flake
Recrystallization solvent: Ethyl acetate-n-hexane
Melting point: 161–162° C.
Form: Free base

TABLE 3

Compound of Example 14

$R^1$: H   $R^2$: H   $R^3$: —$CH_3$   $R^4$: —$CH_3$
OH: at 5-position
—$CH_2NR^3R^4$: at 6-position
Bond between 3- and 4-positions: Single bond
Crystal form: Colorless flake
Recrystallization solvent: Ethyl acetate-n-hexane
Melting point: 189–191° C.   NMR (4)
Form: HCl-salt Compound of Example 15

$R^1$: H   $R^2$: H   $R^3$: —$CH_3$   $R^4$: —$CH_3$
OH: at 6-position
—$CH_2NR^3R^4$: at 7-position
Bond between 3- and 4-positions: Single bond
Crystal form: White powder
Recrystallization solvent: Ethanol
Melting point: 229–230° C. (decomp.)
Form: HCl-salt Compound of Example 16

$R^1$: H   $R^2$: —$CH_3$ (7-position)   $R^3$: —$CH_3$   $R^4$: —$CH_3$
OH: at 6-position
—$CH_2NR^3R^4$: at 5-position
Bond between 3- and 4-positions: Single bond
Crystal form: White powder
Recrystallization solvent: Ethanol
Melting point: 238–239° C. (decomp.)
Form: HCl-salt

TABLE 4

Compound of Example 17

$R^1$: —$CH_2CH$=$C$$\begin{matrix}CH_3\\CH_3\end{matrix}$   $R^2$: —$CH_3$ (7-position)

$R^3$: —$CH_3$   $R^4$: —$CH_3$
OH: at 6-position

TABLE 4-continued

—CH$_2$NR$^3$R$^4$: at 5-position
Bond between 3- and 4-positions: Single bond
Crystal form: White powder
Recrystallization solvent: Ethanol NMR (5)
Melting point: 198–205° C. (decomp.)
Form: HCl-salt
Compound of Example 18

R$^1$: H    R$^2$: —OCH$_2$CH=CH$_2$ (8-position)
R$^3$: —CH$_3$    R$^4$: —CH$_3$
OH: at 5-position
—CH$_2$NR$^3$R$^4$: at 6-position
Bond between 3- and 4-positions: Single bond
Crystal form: White powder
Recrystallization solvent: Ethanol
Melting point: 184–186° C. (decomp.)
Form: HCl-salt
Compound of Example 19

R$^1$: H    R$^2$: —OCH$_2$CH=C(CH$_3$)CH$_3$ (8-position)

R$^3$: —CH$_3$    R$^4$: —CH$_3$
OH: at 5-position
—CH$_2$NR$^3$R$^4$: at 6-position
Bond between 3- and 4-positions: Single bond
Crystal form: Colorless needle-like
Recrystallization solvent: Ethanol-diethyl ether
Melting point: 194–196° C. (decomp.)
Form: HCl-salt

TABLE 5

Compound of Example 20

R$^1$: —CH$_3$    R$^2$: —OCH$_2$CH=CH$_2$ (8-position)
R$^3$: —CH$_3$    R$^4$: —CH$_3$
OH: at 5-position
—CH$_2$NR$^3$R$^4$: at 6-position
Bond between 3- and 4-positions: Single bond
Crystal form: White powder
Recrystallization solvent: Acetone
Melting point: 170–172° C.
Form: HCl-salt
Compound of Example 21

R$^1$: H    R$^2$: H    R$^3$ and R$^4$: —N(piperidine)

OH: at 5-position
—CH$_2$NR$^3$R$^4$: at 6-position
Bond between 3- and 4-positions: Single bond
Crystal form: Colorless granular
Recrystallization solvent: Ethyl acetate NMR (6)
Melting point: 207–217° C.
Form: Free base
Compound of Example 22

R$^1$: H    R$^2$: H    R$^3$ and R$^4$: —N(pyrrolidine)

OH: at 6-position
—CH$_2$NR$^3$R$^4$: at 5-position
Bond between 3- and 4-positions: Double bond

TABLE 5-continued

Crystal form: Pale yellow powder
Recrystallization solvent: Water
Melting point: 242–243° C.
Form: HCl-salt

TABLE 6

Compound of Example 23

R$^1$: H    R$^2$: —CH$_2$CH=CH$_2$ (7-position)

R$^3$ and R$^4$: —N(pyrrolidine)

OH: at 6-position
—CH$_2$NR$^3$R$^4$: at 5-position
Bond between 3- and 4-positions: Single bond
Crystal form: White powder
Recrystallization solvent: Isopropyl alcohol NMR (7)
Melting point: 240–250° C. (decomp.)
Form: HCl-salt
Compound of Example 24

R$^1$: —CH$_2$CH(CH$_3$)CH$_3$    R$^2$: —CH$_2$CH=CH$_2$ (7-position)

R$^3$ and R$^4$: —N(pyrrolidine)

OH: at 6-position
—CH$_2$NR$^3$R$^4$: at 5-position
Bond between 3- and 4-positions: Single bond
Crystal form: White powder
Recrystallization solvent: Ethanol
Melting point: 172–174° C.
Form: HCl-salt
Compound of Example 25

R$^1$: H    R$^2$: —CH$_3$ (6-position)

R$^3$ and R$^4$: —N(pyrrolidine)

OH: at 7-position
—CH$_2$NR$^3$R$^4$: at 8-position
Bond between 3- and 4-positions: Single bond
Crystal form: White powder
Recrystallization solvent: Ethanol
Melting point: 225–227° C. (decomp.)
Form: HCl-salt

TABLE 7

Compound of Example 26

R$^1$: H    R$^2$: —CH$_3$ (8-position)

R$^3$ and R$^4$: —N(piperidine)

OH: at 5-position
—CH$_2$NR$^3$R$^4$: at 6-position

TABLE 7-continued

Bond between 3- and 4-positions: Single bond
Crystal form: Colorless plate
Recrystallization solvent: Ethyl acetate
Melting point: 226–231° C.
Form: Free base
Compound of Example 27

$R^1$: H     $R^2$: —$CH_3$ (8-position)

$R^3$ and $R^4$: 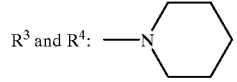

OH: at 5-position
—$CH_2NR^3R^4$: at 6-position
Bond between 3- and 4-positions: Double bond
Crystal form: Colorless needle-like
Recrystallization solvent: Ethanol-water NMR (8)
Melting point: 234–260° C. (decompd.)
Form: HCl-salt
Compound of Example 28

$R^1$: H     $R^2$: —$OCH_2CH=CH_2$ (8-position)

$R^3$ and $R^4$: 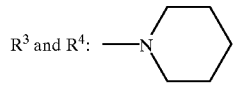

OH: at 5-position
—$CH_2NR^3R^4$: at 6-position
Bond between 3- and 4-positions: Single bond
Crystal form: Pale yellow needle-like
Recrystallization solvent: Ethanol NMR (9)
Melting point: 216–220° C. (decompd.)
Form: HCl-salt

TABLE 8

Compound of Example 29

$R^1$: H     $R^2$: —$OCH_2CH=CH_2$ (8-position)

$R^3$ and $R^4$: 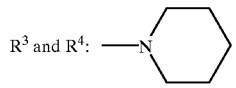

OH: at 5-position
—$CH_2NR^3R^4$: at 6-position
Bond between 3- and 4-positions: Double bond
Crystal form: Pale yellow needle-like
Recrystallization solvent: Ethanol
Melting point: 205–207° C. (decompd.)
Form: HCl-salt
Compound of Example 30

$R^1$: H     $R^2$: —$O(CH_2)_2CH_3$ (8-position)

$R^3$ and $R^4$: 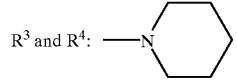

OH: at 5-position
—$CH_2NR^3R^4$: at 6-position
Bond between 3- and 4-positions: Single bond
Crystal form: White powder
Recrystallization solvent: Ethanol
Melting point: 221–224° C. (decompd.)
Form: HCl-salt

TABLE 8-continued

Compound of Example 31

$R^1$: —$CH_3$     $R^2$: —$OCH_2CH=CH_2$ (8-position)

$R^3$ and $R^4$: 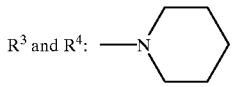

OH: at 5-position
—$CH_2NR^3R^4$: at 6-position
Bond between 3- and 4-positions: Single bond
Crystal form: White powder
Recrystallization solvent: Ethyl acetate
Melting point: 164–167° C.
Form: HCl-salt

TABLE 9

Compound of Example 32

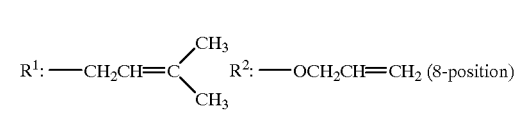

$R^3$ and $R^4$: 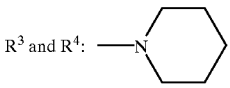

OH: at 5-position
—$CH_2NR^3R^4$: at 6-position
Bond between 3- and 4-positions: Single bond
Crystal form: Colorless flake
Recrystallization solvent: Petroleum ether
Melting point: 77–79° C.
Form: Free base
Compound of Example 33

$R^1$: H     $R^2$: —$OCH_2CH=CH_2$ (8-position)

$R^3$ and $R^4$: 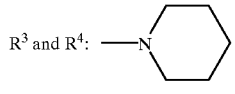

OH: at 5-position
—$CH_2NR^3R^4$: at 6-position
Bond between 3- and 4-positions: Single bond
Crystal form: Colorless flake
Recrystallization solvent: Ethanol
Melting point: 178–179° C.
Form: Free base
Compound of Example 34

$R^1$: H     $R^2$: —$OCH_2CH=CH_2$ (8-position)

$R^3$ and $R^4$: 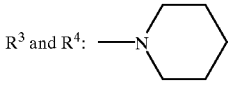

OH: at 5-position
—$CH_2NR^3R^4$: at 6-position
Bond between 3- and 4-positions: Single bond
Crystal form: White powder
Recrystallization solvent: Ethanol
Melting point: 218–220° C.
Form: HCl-salt

TABLE 10

Compound of Example 35

$R^1$: H  $R^2$: —OCH$_3$ (8-position)  $R^3$: —CH$_3$  $R^4$: —CH$_2$OH
OH: at 5-position
—CH$_2$NR$^3$R$^4$: at 6-position
Bond between 3- and 4-positions: Single bond
Crystal form: White powder
Recrystallization solvent: Ethanol
Melting point: 210–212° C.
Form: HCl-salt Compound of Example 36

$R^1$: H  $R^2$: H  $R^3$: —CH$_3$  $R^4$: —CH$_3$
OH: at 7-position
—CH$_2$NR$^3$R$^4$: at 6-position
Bond between 3- and 4-positions: Single bond
Crystal form: White powder
Recrystallization solvent: Ethanol
Melting point: 161–163° C.
Form: HCl-salt Compound of Example 37

$R^1$: —CH$_2$CH=C(CH$_3$)$_2$  $R^2$: —OCH$_2$CH=CH$_2$ (8-position)

$R^3$ and $R^4$: 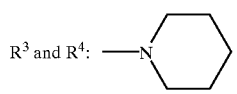

OH: at 5-position
—CH$_2$NR$^3$R$^4$: at 6-position
Bond between 3- and 4-positions: Single bond
Crystal form: White powder
Recrystallization solvent: n-Hexane
Melting point: 79–81° C.
Form: Free base

TABLE 11

Compound of Example 38

$R^1$: H  $R^2$: —OCH$_2$CH=CH$_2$ (5-position)

$R^3$ and $R^4$: 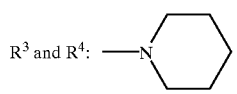

OH: at 8-position
—CH$_2$NR$^3$R$^4$: at 7-position
Bond between 3- and 4-positions: Single bond
Crystal form: White powder
Recrystallization solvent: Ethanol
Melting point: 183–186° C.
Form: HCl-salt Compound of Example 39

$R^1$: H  $R^2$: —OCH$_2$CH=CH$_2$ (8-position)

$R^3$ and $R^4$: 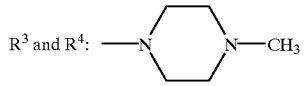

OH: at 5-position
—CH$_2$NR$^3$R$^4$: at 6-position
Bond between 3- and 4-positions: Single bond
Crystal form: White powder
Recrystallization solvent: Ethanol
Melting point: 209–211° C.
Form: HCl-salt

TABLE 11-continued

Compound of Example 40

$R^1$: H  $R^2$: —OCH$_2$CH=CH$_2$ (6-position)
$R^3$: —C$_2$H$_5$  $R^4$: —C$_2$H$_5$
OH: at 5-position
—CH$_2$NR$^3$R$^4$: at 8-position
Bond between 3- and 4-positions: Single bond
Crystal form: White powder
Recrystallization solvent: Ethanol
Melting point: 179–183° C. (decompd.)
Form: HCl-salt

TABLE 12

Compound of Example 41

$R^1$: H  $R^2$: —(CH$_2$)CH$_3$ (6-position)

$R^3$ and $R^4$: 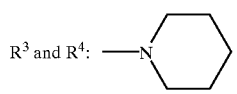

OH: at 5-position
—CH$_2$NR$^3$R$^4$: at 8-position
Bond between 3- and 4-positions: Single bond
Crystal form: White powder
Recrystallization solvent: Ethyl acetate
Melting point: 162–163° C.
Form: Free base Compound of Example 42

$R^1$: H  $R^2$: —OCH$_2$CH=CH$_2$ (8-position)

$R^3$ and $R^4$: 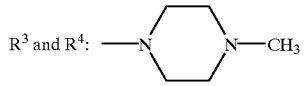—CH$_3$

OH: at 5-position
—CH$_2$NR$^3$R$^4$: at 6-position
Bond between 3- and 4-positions: Single bond
Crystal form: Pale brown plate
Recrystallization solvent: Ethyl acetate-n-hexane
Melting point: 122–123° C.
Form: Free base Compound of Example 43

$R^1$: H  $R^2$: —OCH$_2$CH=CH$_2$ (8-position)
$R^3$: —CH$_2$CH$_2$OH  $R^4$: —CH$_2$CH$_2$OH
OH: at 5-position
—CH$_2$NR$^3$R$^4$: at 6-position
Bond between 3- and 4-positions: Single bond
Crystal form: Colorless needle-like
Recrystallization solvent: Ethyl acetate-n-hexane
Melting point: 106.2° C.
Form: Free base

TABLE 13

Compound of Example 44

$R^1$: H  $R^2$: —OCH$_2$CH=CH$_2$ (8-position)
$R^3$: —CH$_2$CH$_2$OH  $R^4$—CH$_2$CH$_3$
OH: at 5-position
—CH$_2$NR$^3$R$^4$: at 6-position
Bond between 3- and 4-positions: Single bond
Crystal form: Colorless needle-like
Recrystallization solvent: Ethyl acetate-n-hexane
Melting point: 86–87° C.
Form: Free base

TABLE 13-continued

Compound of Example 45

R$^1$: H    R$^2$: —OCH$_2$CH=CH$_2$ (8-position)

R$^3$ and R$^4$: 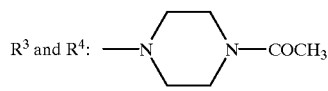

OH: at 5-position
—CH$_2$NR$^3$R$^4$: at 6-position
Bond between 3- and 4-positions: Single bond
Crystal form: White powder
Recrystallization solvent: Ethyl acetate
Melting point: 184–186° C.
Form: Free base Compound of Example 46

R$^1$: H  R$^2$: 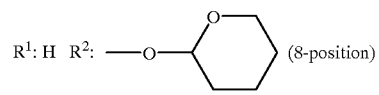 (8-position)

R$^3$: —CH$_3$    R$^4$: —CH$_3$
OH: at 5-position
—CH$_2$NR$^3$R$^4$: at 6-position
Bond between 3- and 4-positions: Single bond
Crystal form: White powder
Recrystallization solvent: Ethyl acetate
Melting point: 152–153° C.
Form: Free base

TABLE 14

Compound of Example 47

R$^1$: H  R$^2$: 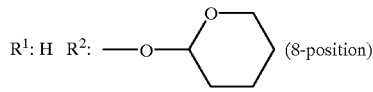 (8-position)

R$^3$ and R$^4$: 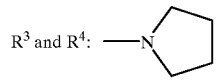

OH: at 5-position
—CH$_2$NR$^3$R$^4$: at 6-position
Bond between 3- and 4-positions: Single bond
Crystal form: White powder
Recrystallization solvent: Ethyl acetate
Melting point: 136–137° C.
Form: Free base NMR spectra of compounds (1)–(9) in Examples 9, 10, 11, 14, 17, 21, 23, 27 and 28 are:

(1) $^1$H-NMR (CDCl$_3$) δ ppm: 1.10 (6H, t), 2.10 (3H, s), 2.55–2.65 (6H, m), 2.94 (2H, t), 3.68 (2H, s), 6.62 (1H, s), 7.26 (1H, s).

(2) $^1$H-NMR (CDCl$_3$) δ ppm: 1.04 (6H, t), 2.18 (3H, s), 2.48 (4H, q), 2.56 (2H, t), 2.93 (2H, t), 3.53 (1H, br), 6.70 (1H, s), 10.25 (1H, s).

(3) $^1$H-NMR (CDCl$_3$) δ ppm: 2.31 (3H, s), 2.34 (6H, s), 3.64 (2H, s), 6.55 (1H, d), 6.89 (1H, s), 8.17 (1H, d), 9.68 (1H, br).

(4) $^1$H-NMR (DMSO-d$_6$) δ ppm: 1.60 (6H, s), 2.52 (2H, dd), 2.80 (2H, dd), 4.42–4.46 (2H, m), 5.13 (1H, t), 5.24 (1H, dd), 5.35 (1H, dd), 5.96–6.11 (1H, m), 6.60 (1H, d), 6.69 (1H, d).

(5) $^1$H-NMR (DMSO-d$_6$) δ ppm: 1.66 (3H, s), 1.76 (3H, s), 2.22 (3H, s), 2.51 (2H, t), 2.74 (6H, s), 2.92 (2H, t), 3.35 (2H, s), 4.33 (2H, d), 5.04 (1H, t), 6.88 (1H, s), 8.98 (1H, s), 9.87 (1H, br).

(6) $^1$H-NMR (CDCl$_3$) δ ppm: 1.40–1.50 (6H, m), 2.15–2.80 (6H, m), 2.94 (2H, t), 3.60 (2H, s), 6.35 (1H, d), 6.74 (1H, d), 8.58 (1H, S), 9.96 (1H, br).

(7) $^1$H-NMR (DMSO-d$_6$) δ ppm: 1.80–2.15 (4H, m), 2.43 (2H, t), 3.05–3.36 (4H, m), 5.02 (1H, dd), 5.09 (1H, dd), 5.83–5.99 (1H, m), 6.71 (1H, s), 8.76 (1H, s), 9.90 (1H, s), 10.19 (1H, br).

(8) $^1$H-NMR (DMSO-d$_6$) δ ppm: 1.25–1.85 (6H, m), 2.32 (3H, s), 2.91 (2H, br), 3.36 (2H, br), 4.29 (2H, s), 6.48 (1H, d) 7.44 (1H, s), 8.25 (1H, d), 10.9 (1H, br) 10.85 (1H, s).

(9) $^1$H-NMR (DMSO-d$_6$) δ ppm: 1.12–1.95 (6H, m), 2.43 (2H, t), 2.75–3.00 (4H, br), 3.27 (2H, br), 4.17 (2H, s), 4.56 (2H, d), 5.24 (1H, dd), 5.44 (1H, dd), 6.02–6.17 (1H, m), 7.15 (1H, s), 8.85 (1H, s) 9.03 (1H, s), 10.18 (1H, br).

Pharmaceutical preparation example 1

| | |
|---|---|
| 5-Hydroxy-6-diethylaminomethyl-8-methyl-3,4-dihydro-2(1H)-quinolinone (compound of the present invention) | 5 mg |
| Starch | 132 mg |
| Magnesium stearate | 18 mg |
| Lactose | 45 mg |
| Total | 200 mg |

By using a conventional procedure, each tablet containing the above-mentioned formulation was prepared.

Pharmaceutical preparation example 2

| | |
|---|---|
| 5-Hydroxy-6-(1-piperidinyl)methyl-8-allyloxy-2(1H)-quinolinone (compound of the present invention) | 500 mg |
| Polyethylene glycol (M.W. 4,000) | 0.3 g |
| Sodium chloride | 0.9 g |
| Polyoxyethylene sorbitan monooleate | 0.4 g |
| Sodium metabisulfite | 0.1 g |
| Methyl paraben | 0.18 g |
| Propyl paraben | 0.02 g |
| Distilled water for injection | 100 ml |

The above mentioned parabens, sodium metabisulfite and sodium chloride were dissolved in the above-mentioned distilled water at 80° C. under stirring. The solution thus obtained was cooled to 40° C., then the compound of the present invention, polyethylene glycol and polyoxyethylene sorbitan monooleate were dissolved therein in this order. The volume of this solution was adjusted to the final volume by adding distilled water for injection, then the solution was subjected to sterile filtration by using a suitable filter paper. 1 mt each of the solution thus obtained was filled in an ampoule separately to make injection preparation.

Pharmacological tests

Pharmacological tests of carbostyril derivatives represented by the general formula (1) of the present invention were conducted by test methods as explained below with the following results.

(1) DPPH free radical extinction activity test

The test was conducted by procedures according to the method by Marsden S. Blois [Nature, Vol. 26, 1199–1200, (1958)].

Into 0.5 ml of 200 mM of acetic acid buffer solution (pH 5.5) were added 0.5 ml of distilled water, 0.5 ml of ethanol and 5 µl of 10 mM of the test compound solution (an ethanol solution, a dimethylformamide solution or an aqueous solution), and stirred at 30° C. for 5 minutes. To this mixed solution was added 1.5 ml of an ethanol solution of 250 µM of 1,1-diphenyl-2-picrylhydrazyl (DPPH), this mixture was incubated at 30° C. for 30 minutes. After the incubation, the optical absorbance (at 517 nm) of this reaction mixture was measured, and the number of captured free radicals of DPPH was calculated from the ratio of optical absorbance of test compound and that of α-tocopherol (standard substance: the number of captured free radicals: 2) by the following formula:

Number of captured free radicals of DPPH performed by test sample=$[(A) \times 2]/(B)$

[wherein
(A): optical absorbance of the test sample, and
(B): optical absorbance of α-tocopherol].
The test results are shown in Table 15.

TABLE 15

| Test compound | Number of captured free radicals of DPPH |
| --- | --- |
| Compound of Example 9 | 1 |
| Compound of Example 13 | 1 |
| Compound of Example 18 | 1.5 |
| Compound of Example 22 | 1.5 |
| Compound of Example 23 | 3 |
| Compound of Example 25 | 1 |
| Compound of Example 28 | 2 |
| Compound of Example 30 | 2 |
| Compound of Example 32 | 1 |
| Compound of Example 33 | 1.5 |
| Compound of Example 35 | 1.5 |
| Compound of Example 47 | 3.5 |

(2) Effect for preventing skin sunburn caused by UV rays irradiation (in vivo)

This test is an experimental model of quantitative evaluation of effect for preventing skin sunburn, caused by UV rays irradiation, performed by the test compound. [Test was conducted by a modified method according to the procedures of J. Dermatol. Vol. 17, pp. 595–598, (1990).]

Hairs on the back of an albino guinea pig (Hartley strain, female, age of 7–8 weeks) were shaved by use of an electric hair clipper and an electric shaver. Next day, the guinea pig was fixed on a Bowlman cage, a piece of shading tape (a plaster for patch test) having 4 circular holes of 1.5 cm in diameter was put on the shaved portion of the skin, and predetermined 2 sections of UV rays irradiation. One section (reference section) was coated with 10 µl of a solvent (water or 50% ethanol-water solution). Another section (test section) was coated with 10 µl of 3% test compound solution (aqueous or 50% ethanol-water solution). 30 Minutes after the coating, UV rays of 1.3–1.5 mW/cm$^2$ in strength was irradiated for 30 minutes by use of a fluorescent lamp of healthy light (TOSHIBA FL-20•SE) as a light source. 24 Hours after the irradiation, the reference section (coated with the solvent only) and the test section (coated with test compound solution) were observed respectively, and the erythrochromia (Δa value) on both reference section and test section were measured by use of a color difference meter (OFC-300A Type, mfd. by NIHON DENSHOKU KOGYO CO., LTD). The inhibitory ratio of skin erythema (sunburn) performed by the test compound was calculated from the following formula.

Inhibitory ratio of skin erythema (sunburn) (%)={1−[(C)/(D)]}×100

[wherein
(C): Δa Value of test section of skin coated with test compound solution,
(D): Δa Value of reference section of skin coated with the solvent only, and
Δa value: difference of skin erythema on the portion irradiated with UV rays].
The test results are shown in Table 16.

TABLE 16

| Test compound | (C) | (D) | Inhibitory ratio of skin erythema (%) |
| --- | --- | --- | --- |
| Compound of | | | |
| Example 9 | 4.69 ± 1.62** | 7.61 ± 0.99 | 38 |
| Example 13 | 3.93 ± 0.92** | 6.71 ± 1.21 | 42 |
| Example 18 | 3.87 ± 2.45** | 7.50 ± 1.24 | 51 |
| Example 22 | 5.51 ± 2.32** | 8.52 ± 1.33 | 37 |
| Example 23 | 4.46 ± 1.28** | 8.27 ± 1.46 | 46 |
| Example 25 | 3.31 ± 2.00** | 8.87 ± 1.66 | 64 |
| Example 28 | 1.13 ± 0.58** | 5.03 ± 1.03 | 78 |
| Example 30 | 4.73 ± 1.94** | 7.91 ± 1.31 | 40 |
| Example 32 | 2.17 ± 0.97** | 6.07 ± 0.97 | 64 |
| Example 33 | 3.96 ± 1.02** | 7.73 ± 1.11 | 49 |
| Example 35 | 3.61 ± 2.91 * | 6.72 ± 1.78 | 51 |
| Example 47 | 0.88 ± 0.29** | 4.08 ± 1.57 | 76 |

*: $p < 0.05$,
**: $p < 0.01$ (One way ANOVA followed by two-tailed Dunnett's test)

(3) Effect for preventing skin pigmentation caused by UV rays irradiation

This is an experimental model of quantitative evaluation of effect for preventing skin pigmentation caused by UV rays irradiation performed by test compound. [Test was conducted by a modified method according to procedures of J. Dermatol. Vol. 17, pp. 595–598,(1990).]

Hairs on the back of a colored guinea pig (A-1 strain, female, age of 8–10 weeks) were shaved and the body of guinea pig was fixed on a Bowlman cage, and predermined 2 sections of UV rays irradiation. One section (reference section) was coated with 10 µl/cm$^2$ of a solvent (water or 50% ethanol-water solution). Another section (test section) was coated with 10 µl/cm$^2$ of 3% test compound solution (aqueous or 50% ethanol-water solution). 30 Minutes after the coating, UV rays of intensity of 0.838 mV/cm was irradiated for 50 minutes by use of a solar simulator (WXS-200s-20: mfd. by WAKOMU SEISAKUSHO) in which a xenone lamp of 150W (KXL-2003F: mfd. by WAKOMU SEISAKUSHO) was installed as a light source. Intensity of the light (mV/cm$^2$) was measured by using a photometer (EPPLEY Thermopile 28571J3: mfd. by WAKOMU SEISAKUSHO). 14 Days after the irradiation, the brightness (ΔL value) of the skin of reference section and that of the test section coated with test compound solution were measured by using a color difference meter (Degital color meter OFC-300A type: mfd. by NIHON DENSHOKU KOGYO). The inhibitory ratio of the skin pigmentation (%) performed by the test compound was calculated from the following formula.

Inhibitory ratio of skin pigmentation (%)={1−[(E)/(F)]}×100

[wherein
(E): ΔL value of brightness of the skin coated with test compound solution (test section),
(F): ΔL value of brightness of the skin coated the solvent (reference section), and
ΔL value: difference of brightness of the skin between the portion without irradiated and the portion irradiated with UV rays].

The results are shown in Table 17.

TABLE 17

| Test compound | (E) | (F) | Inhibitory ratio of skin pigmentation (%) |
|---|---|---|---|
| Compound of | | | |
| Example 18 | −3.53 ± 1.24* | −6.92 ± 1.61 | 49 |
| Example 25 | −5.02 ± 2.02 | −8.04 ± 2.43 | 38 |
| Example 28 | −4.51 ± 1.87** | −7.90 ± 1.30 | 43 |
| Example 30 | −3.40 ± 1.18** | −6.77 ± 1.79 | 50 |
| Example 32 | −3.37 ± 2.36 | −5.77 ± 2.36 | 42 |
| Example 33 | −2.61 ± 2.98* | −5.77 ± 2.36 | 55 |
| Example 35 | −4.44 ± 2.17 | −6.84 ± 3.09 | 35 |
| Example 47 | −4.89 ± 1.24** | −7.90 ± 2.26 | 38 |

*: $p < 0.05$,
**$p < 0.01$ (One way ANOVA followed by two-tailed Dunnett's test)

(4) Skin sensitization test [Adjuvant and strip test: J. Invest. Dermatol., Vol. 76, pp 498–501, (1981)]

This test was used as experimental model for evaluating the existence of toxicity of photosensitization to the skin performed by the test compounds.

(i) Procedure for inducing photosensitization

Albino guinea pigs (Hertley strain, female, age of 5–6 weeks) were used. Hairs of the nuchal area of the guinea pig were shaved, and designated the test sample coating section having 2×4 cm in size. At the four corners of the test sample coating section, 0.1 ml each of E-FCA (an emulsion consisting of the same volume each of Freund's complete adjuvant with sterilized distilled water) were intracutaneouly injected. The coating section was subjected to striping repeatedly by use of Cellophane tape until the section turned to slightly erythema, then 0.1 ml of test compound solution (aqueous or 50% ethanol-water solution) of 3% in concentration was open-coated on the section. 30 Minutes after the coating, UV rays of about 10 J/cm² in dosage was irradiated by use of a fluorescent lamp of healthy light (TOSHIBA FL-20S-BLB) as a light source. The above-mentioned procedure was carried out once a day, and continuously conducted for 5 days, provided that E-FCA was administered only on the first day.

(ii) Procedure for introducing sensitization

3 Weeks after the beginning of induction period of photosensitization, the covering hairs on the back of guinea pig were shaved, and determined a circular section, having 1.5 cm in diameter, for coating test samples, and 20 μl of test compound solution (aqueous or 50% ethanol-water solution) of 3% in concentration was open-coated on the section. The test sample coated section was observed 24 hours and 48 hours, and examined existences of skin reaction (erythema and edema). In case of skin reaction was appeared, then it was determined as positive reaction in skin sensitization which was defined as a positive ratio (%) calculated from the following formula.

Positive ratio (%)=[(G)/(H)]×100

[wherein
(G): Number of positive reactions in skin sensitization and
(H): Number of total animal tests].
The results are shown in Table 18.

TABLE 18

| Test compound | Positive ratio (%) |
|---|---|
| Compound of | |
| Example 9 | 0 |
| Example 13 | 0 |
| Example 18 | 0 |
| Example 22 | 0 |
| Example 25 | 0 |
| Example 28 | 0 |
| Example 30 | 0 |
| Example 32 | 0 |
| Example 33 | 0 |
| Example 35 | 0 |
| Example 47 | 0 |

What is claimed is:

1. A carbostyril derivative or a salt thereof represented by the general formula (1),

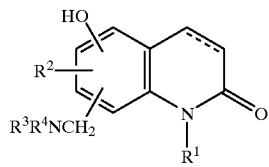

(1)

(wherein $R^1$ is a hydrogen atom, a lower alkyl group or a lower alkenyl group; $R^2$ is a hydrogen atom, a lower alkyl group, a lower alkoxy group, a lower alkenyloxy group, a lower alkenyl group or a tetrahydropyranyloxy group; $R^3$ and $R^4$ are the same or different from each other and are lower alkyl groups which may have hydroxyl groups as substituents; further $R^3$ and $R^4$ may form, together with the adjacent nitrogen atom, further with or without an additional nitrogen atom, sulfur atom or oxygen atom, a 5- or 6-membered saturated heterocyclic group which may have substituents selected from the group consisting of a lower alkyl group and a lower alkanoyl group; the carbon—carbon bond between 3- and 4-positions in the carbostyril skeleton is a single bond or double bond; provided that when $R^3$ and $R^4$ are lower alkyl groups at the same time, then $R^2$ should be neither a hydrogen atom, a lower alkyl group nor a lower alkoxy group).

2. The carbostyril derivative or a salt thereof according to claim 1, wherein $R^1$ is a hydrogen atom; $R^2$ is a hydrogen atom, a lower alkyl group or a lower alkoxy group.

3. The carbostyril derivative or a salt thereof according to claim 1, wherein $R^1$ is a hydrogen atom; $R^2$ is a lower alkenyloxy group, a lower alkenyl group or a tetrahydropyranyloxy group.

4. The carbostyril derivative or a salt thereof according to claim 1, wherein $R^1$ is a lower alkyl group; $R^2$ is a hydrogen atom, a lower alkyl group or a lower alkoxy group.

5. The carbostyril derivative or a salt thereof according to claim 1, wherein $R^1$ is a lower alkyl group; $R^2$ is a lower alkenyloxy group, a lower alkenyl group or a tetrahydropyranyloxy group.

6. The carbostyril derivative or a salt thereof according to claim 1, wherein $R^1$ is a lower alkenyl group; $R^2$ is a hydrogen atom, a lower alkyl group or a lower alkoxy group.

7. The carbostyril derivative or a salt thereof according to claim 1, wherein $R^1$ is a lower alkenyl group; $R^2$ is a lower alkenyloxy group, a lower alkenyl group or a tetrahydropyranyloxy group.

8. The carbostyril derivative or a salt thereof according to claim 1, wherein the hydroxyl group is substituted at 5-position in the carbostyril skeleton; $R^2$ is substituted at 6-position; and the group of the formula —$CH_2NR^3R^4$ is substituted at 8-position in the carbostyril skeleton.

9. The carbostyril derivative or a salt thereof according to claim 1, wherein the carbon—carbon bond between 3- and 4-positions in the carbostyril skeleton is a single bond.

10. The carbostyril derivative or a salt thereof according to claim 1, wherein the carbon—carbon bond between 3- and 4-positions in the carbostyril skeleton is a double bond.

11. The carbostyril derivative or a salt thereof according to any one of claims 2–7, wherein $R^3$ and $R^4$ are lower alkyl groups which may have hydroxyl groups as substituents.

12. The carbostyril derivative or a salt thereof according to any one of claims 2–7, wherein $R^3$ and $R^4$ form, together with the adjacent nitrogen atom and further with or without an additional nitrogen atom, sulfur atom or oxygen atom, a 5- or 6-membered saturated heterocyclic group.

13. A compound according to claim 1, which is 3,4-dihydro-8-allyloxy-5-hydroxy-6-(1-piperidinyl)methyl-2(1H)-quinolinone.

14. A compound according to claim 1, which is 3,4-dihydro-8-allyloxy-5-hydroxy-6-morpholinomethyl-2(1H)-quinolinone.

15. A compound according to claim 1, which is 3,4-dihydro-8-propoxy-5-hydroxy-6-(1-piperidinyl)methyl-2(1H)-quinolinone.

16. A compound according to claim 1, which is 3,4-dihydro-8-methyl-5-hydroxy-6-(1-piperidinyl)methyl-2(1H)-quinolinone.

17. An agent for preventing and treating dermatopathy or dermatitis containing at least one selected from the group consisting of the carbostyril derivative and salt thereof claimed in claim 1.

18. The agent for preventing and treating dermatopathy or dermatitis according to claim 17, wherein the carbostyril derivative is 3,4-dihydro-8-allyloxy-5-hydroxy-6-(1-piperidinyl)methyl-2(1H)-quinolinone, 3,4-dihydro-8-allyloxy-5-hydroxy-6-morpholinomethyl-2(1H)-quinolinone, 3,4-dihyro-8-propoxy-5-hydroxy-6-(1-piperidinyl)methyl-2(1H)-quinolinone, 3,4-dihydro-8-methyl-5-hydroxy-6-(1-piperidinyl)methyl-2(1H)-quinolinone or 3,4-dihydro-5-hydroxy-6-diethylaminomethyl-2(1H)-quinolinone.

19. An agent for inhibiting skin erythema and/or skin pigmentation containing at least one selected from the group consisting of the carbostyril derivative and salt thereof as claimed in claim 1.

20. The agent for inhibiting skin erythema or skin pigmentation according to claim 19, wherein the carbostyril derivative is 3,4-dihydro-8-allyloxy-5-hydroxy-6-(1-piperidinyl)methyl-2(1H)-quinolinone, 3,4-dihydro-8-allyloxy-5-hydroxy-6-morpholinomethyl-2(1H)-quinolinone, 3,4-dihyro-8-propoxy-5-hydroxy-6-(1-piperidinyl)methyl-2(1H)-quinolinone, 3,4-dihydro-8-methyl-5-hydroxy-6-(1-piperidinyl)methyl-2(1H)-quinolinone or 3,4-dihydro-5-hydroxy-6-diethylaminomethyl-2(1H)-quinolinone.

21. A method for inhibiting skin erythema and/or skin pigmentation comprising administering a medicament containing at least one compound selected from the group consisting of the carbostyril derivative and salt thereof represented by the general formula,

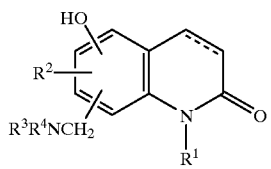

(wherein $R^1$ is hydrogen atom, a lower alkyl group or a lower alkenyl group; $R^2$ is a hydrogen atom, a lower alkyl group, a lower alkoxy group, a lower alkenyloxy group, a lower alkenyl group or a tetrahydropyranyloxy group; $R^3$ and $R^4$ are the same or different from each other and are lower alkyl groups which may have hydroxyl groups as substituents; further $R^3$ and $R^4$ may form, together with the adjacent nitrogen atom and further with or without an additional nitrogen atom, sulfur atom or oxygen atom, a 5- or 6-membered saturated heterocyclic group which may have substituents selected from the group consisting of a lower alkyl group and a lower alkanoyl group; the carbon—carbon bond between 3- and 4-positions in the carbostyril skeleton is a single bond or double bond; provided that when $R^3$ and $R^4$ are lower alkyl groups at the same time, then $R^2$ should be neither a hydrogen atom, a lower alkyl group nor a lower alkoxy group).

22. Process for preparing a carbostyril derivative represented by the general formula (1),

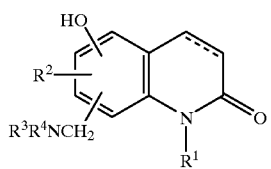

(1)

(wherein $R^1$ is hydrogen atom, a lower alkyl group or a lower alkenyl group; $R^2$ is a hydrogen atom, a lower alkyl group, a lower alkoxy group, a lower alkenyloxy group, a lower alkenyl group or a tetrahydropyranyloxy group; $R^3$ and $R^4$ are the same or different from each other and are lower alkyl groups which may have hydroxyl groups as substituents; further $R^3$ and $R^4$ may form, together with the adjacent nitrogen atom and further with or without an additional nitrogen atom, sulfur atom or oxygen atom a 5- or 6-membered saturated heterocyclic group which may have substituents selected from the group consisting of a lower alkyl group and a lower alkanoyl group; the carbon—carbon bond between 3- and 4-positions in the carbostyril skeleton is a single bond or double bond; provided that when $R^3$ and $R^4$ are lower alkyl groups at the same time, then $R^2$ should be neither a hydrogen atom, a lower alkyl group nor a lower alkoxy group) by reacting a compound of the general formula (3),

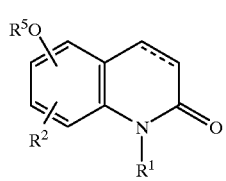

(3)

(wherein $R^1$, $R^2$ and the carbon—carbon bond between 3- and 4-positions in the carbostyril skeleton are the same as defined above; and $R^5$ is a hydrogen atom, a tetrahydropyranyl group or a lower alkanoyl group) with a compound of the general formula (4),

 (4)

(wherein $R^3$ and $R^4$ are the same as defined above), or a compound of the general formula (5),

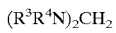 (5)

(wherein $R^3$ and $R^4$ are the same as defined above).

23. Process for preparing a carbostyril derivative represented by the general formula (1b),

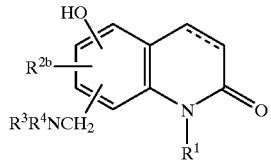 (1b)

(wherein $R^1$, $R^3$, $R^4$ and the carbon—carbon bond between 3- and 4-positions in the carbostyril skeleton are the same as defined in claim 22; and $R^{2b}$ is a lower alkyl group or a lower alkyloxy group; provided that when $R^3$ and $R^4$ are lower alkyl groups at the same time, then $R^{2b}$ should be neither a hydrogen atom a lower alkyl group nor a lower alkoxy group) by reducing a compound represented by the general formula (1a),

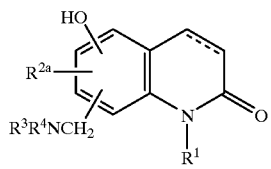 (1a)

(wherein $R^1$, $R^3$, $R^4$ and the carbon—carbon bond between 3- and 4-positions in the carbostyril skeleton are the same as defined in claim 22; and $R^{2a}$ is a lower alkenyl group or a lower alkenyloxy group).

24. Process for preparing a carbostyril derivative represented by the general formula (1d),

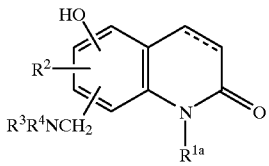 (1d)

(wherein $R^2$, $R^3$, $R^4$ and the carbon—carbon bond between 3- and 4-positions in the carbostyril skeleton are the same as defined in claim 22; and $R^{1a}$ is a lower alkyl group or a lower alkenyl group; provided that when $R^3$ and $R^4$ are lower alkyl groups at the same time, then $R^2$ should be neither a hydrogen atom, a lower alkyl group nor a lower alkoxy group) by reacting a compound of the general formula (1c),

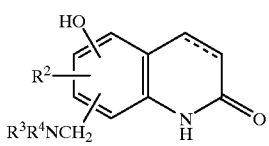 (1c)

(wherein $R^2$, $R^3$, $R^4$ and the carbon—carbon bond between 3- and 4-positions in the carbostyril skeleton are the same as defined in claim 22) with a compound of the general formula (8),

 (8)

(wherein $R^{1a}$ is the same as defined above; and X is a halogen atom).

* * * * *